US005693779A

United States Patent [19]

Moos, Jr. et al.

[11] Patent Number: 5,693,779
[45] Date of Patent: Dec. 2, 1997

[54] PRODUCTION AND USE OF ANTI-DORSALIZING MORPHOGENETIC PROTEIN

[75] Inventors: Malcolm Moos, Jr., Bethesda; Marie Krinks; Shouwen Wang, both of Rockville, all of Md.

[73] Assignee: The United States of America as represented by the Department of Health and Human Services, Washington, D.C.

[21] Appl. No.: 335,583

[22] Filed: Nov. 8, 1994

[51] Int. Cl.$^6$ .................... C07H 21/04; C07K 14/51; C12N 15/12; A61K 38/18
[52] U.S. Cl. .................... 536/23.5; 530/399; 930/120; 514/12
[58] Field of Search .................... 536/23.5; 530/399; 930/120; 514/12

[56] References Cited

U.S. PATENT DOCUMENTS 5,279,966 1/1994 Jessell et al. .................... 530/399

OTHER PUBLICATIONS

Harland et al "The Transforming Growth Factor β Family ..." *PNAS* 91(22):10243–10246 (Oct. 1994).
Basler et al, "Control of Cell Pattern in the Neural Tube..." *Cell* 73:687–702 (May 1993).
Christian et al, "Xwnt-8 Modifies the Character of Mesoderm..." *EMBO J* 11(1):33–4 (1992).
Smith et al, "Injected Xwnt-8 RNA Acts Early in Xenopus ..." *Cell* 67:753–765 (Nov. 1991).
Berkow et al, *The Merck Manual*, pp. 1387–1388, 1606–1607, 1961–1962.

*Primary Examiner*—Vasu S. Jagannathan
*Assistant Examiner*—David Romeo
*Attorney, Agent, or Firm*—Knobbe, Martens, Olson & Bear, LLP

[57] ABSTRACT

An isolated polynucleotide of anti-dorsalizing morphogenetic protein (ADMP-1) is obtained from Xenopus. The protein is most closely related to human BMP-3. ADMP-1 functions as a modulator for dorsalizing influences, and prevents syndromes involving inappropriate proliferation of tissues.

6 Claims, 11 Drawing Sheets

FIG. 1

| | | | | | | | |
|---|---|---|---|---|---|---|---|
| ADMP-1 | QQRHPLYVDF | EEIGWSGWII | SPRGYNAYHC | KGSCPFPLGQ | NMRPT----N | | 46 |
| BMP-3 | CARRYLKVDF | ADIGWSEWII | SPKSFDAYYC | SGACQFPMPK | SLKPS----N | | 46 |
| BMP-2 | CKRHPLYVDF | SDVGWNDWIV | APPGYHAFYC | HGECPFPLAD | HLNST----N | | 46 |
| BMP-4 | CRRHSLYVDF | SDVGWNDWIV | APPGYQAFYC | HGDCPFPLAD | HLNST----N | | 46 |
| Vg1 | CKKRHLYVEF | KDVGWQNWVI | APQGYMANYC | YGECPYPLTE | ILNGS----N | | 46 |
| GDF-1 | CRARRLYVSF | REVGWHRWVI | APRGFLANYC | QGQCALPVAL | SGSGGPPALN | | 50 |
| BMP-5 | CKKHELYVSF | RDLGWQDWII | APEGYAAFYC | DGECSFPLNA | HMNAT----N | | 46 |
| BMP-7 | CKKHELYVSF | RDLGWQDWII | APEGYAAYYC | EGECAFPLNS | YMNAT----N | | 46 |
| BMP-6 | CRKHELYVSF | QDLGWQDWII | APKGYAANYC | DGECSFPLNA | HMNAT----N | | 46 |
| 60A | CQMQTLYIDF | KDLGWHDWII | APEGYGAFYC | SGECNFPLNA | HMNAT----N | | 46 |
| dpp | CRRHSLYVDF | SDVGWDDWIV | APLGYDAYYC | HGKCPFPLAD | HFNST----N | | 46 |
| GDF-5 | CSRKALHVNF | KDMGWDDWII | APLEYEAFHC | EGLCEFPLRS | HLEPT----N | | 46 |
| activin B | CR-QQFYIDF | RLIGWNDWII | APAGYYGNYC | EGSCPAYLAG | VPGSASSFHT | | 49 |
| dorsalin | CRRTSLHVNF | KEIGWDSWII | APKDYEAFEC | KGGCFFPLTD | NVTPT----K | | 46 |
| nodal | CRRVKFQVDF | NLIGWGSWII | YPKQYNAYRC | EGECPNPVGE | EFHPT----N | | 46 |
| Consensus | C.R..LYVDF | .D.GW.DWII | AP..GY.A.YC | .G.C.FPL.. | ..N..T----N | | 50 |

| | | | | | | | |
|---|---|---|---|---|---|---|---|
| ADMP-1 | HATVQSIINA | LKLTKGVSSP | CCVPDKLFSI | NLLYFDDDEN | -VVLKQYDDM | VAGSCGCH- | 103 |
| BMP-3 | HATIQSIVRA | VGVVPGIPEP | CCVPEKMSSL | SILFFDENKN | -VVLKVYPNM | TVESCACR- | 103 |
| BMP-2 | HAIVQTLVNS | VN--SKIPKA | CCVPTELSAI | SMLYLDENEK | -VVLKNYQDM | VVEGCGCR- | 101 |
| BMP-4 | HAIVQTLVNS | VN--SSIPKA | CCVPTELSAI | SMLYLDEYDK | -VVLKNYQEM | VVEGCGCR- | 101 |
| Vg1 | HAILQTLVHS | IE-PEDIPLP | CCVPTKMSPI | SMLFYDNNDN | -VVLRHYENM | AVDECGCR- | 102 |
| GDF-1 | HAVLRALMHA | AA-PGAADLP | CCVPARLSPI | SVLFFDNSDN | -VVLRQYEDM | VVDECGCR- | 106 |
| BMP-5 | HAIVQTLVHL | MF-PDHVPKP | CCAPTKLNAI | SVLYFDDSSN | -VILKKYRNM | VVRSCGCHI | 103 |
| BMP-7 | HAIVQTLVHF | IN-PETVPKP | CCAPTQLNAI | SVLYFDDSSN | -VILKKYRNM | VVRACGCH- | 102 |
| BMP-6 | HAIVQTLVHL | MN-PEYVPKP | CCAPTKLNAI | SVLYFDDSSN | -VILKKYRNM | VVRACGCHE | 103 |
| 60A | HAIVQTLVHL | LE-PKKVPKA | CCAPTRLGAL | PVLYHLNDEN | -VNLKKYRNM | IVKSCGCH- | 103 |
| dpp | HAVVQTLVNS | MN-PGKVPKA | CCVPTQLDSV | AMLYLNDQST | -VVLKNYQEM | TVVGCGCR- | 102 |
| gdf-5 | HAVIQTLMNS | MD-PESTPPT | CCIPTKLSTM | SILFIDSANN | -VVYKQYEDM | VVESCGCR- | 102 |
| activin B | AVVNQYRMRG | LN-PGTV-NS | CCIPTKLSTM | SMLYFDDEYN | -IVKRDVPNM | IVDECGCA- | 104 |
| dorsalin | HAIVQTLVHL | QN-PKKASKA | CCVPTKLDAI | SILYKDDAGV | PTLIYNYEGM | KVAECGCR- | 103 |
| nodal | HAYIQSLLKR | YQ-PHRVPST | CCAPVKTKPL | SMLYVDNGRV | --LLEHHKDM | IVEECGCL- | 101 |
| Consensus | HAIVQTLV.. | ...P...VPKP | CCVPIKL... | I S..LY.D...N | -VVLK.Y..M | VV..CGCR- | 109 |

SEQUENCE LISTING ( 1 ) GENERAL INFORMATION:

( i i i ) NUMBER OF SEQUENCES: 56

( 2 ) INFORMATION FOR SEQ ID NO:1:

( i ) SEQUENCE CHARACTERISTICS:
        ( A ) LENGTH: 1170 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:1:

```
ATGGACCTTA GGAAGATGTT GGGTTTTATA TTTCTGTTTT TTATCATACA AGAATGTACC    60
TCCAGACCTA CTGATATGGT GGACAGTACT GACCTTGAAT TAGAAGACCC TGAGCTAGTA   120
AGAGCTGAAG CCCTGAAAAG ACTATTGGAA GTGTTTGGTA TTGAGGAACC ACCACAGCCT   180
CTTCAGCATG TCAAGCAGCC ACCTCAGTAT ATGGTGGACC TTTACAACAC AGTAGCTGAT   240
GAAGATGGTG TAACCAAGGA CCCAGACCTT CTAGAAGGAA ATACAGTCAG GAGTTTTTTT   300
GATAAAATTC ACAGCGACCA TATGCATTTC TTGTTTAACC TCTGGACTGT GGCCAGAAAC   360
GAGAAGATTC TAACAGCAGA ACTTCATCTT TTTAAATTAA AACCAAGGCC TTCCGAGCAA   420
GCTTACTTCA AAAGGCACCA CTTCTGCCAG ATAAGTGTCT ATATGGTCCT AGATAAAAAT   480
AAGATACAGT TGCCACAAGG AAGAAAACTG CTATCATCAA AACTTGTACC AATTCATTCT   540
TCAGGATGGG AAGTGTTTTC TATAACCCAA GCTGTCCGAG CTTGGAATGA TGAAAGTGCT   600
AATCATGGCA TCCTTGTAAC TGTCCGAAAT CTGGGAGGAG CACAAGTTGA TCCAAACATC   660
ATCCGTTTTG CATCTGGTAG AGATCACCAT GAAAGCAAAC AGCCCATGCT GGTTCTATTC   720
ACTGATGATG GAAGGAGAGG AATTGTCTCA GTAAACAATC AGCCTGATGA CCAATTAATG   780
CCCCTACCAA ATGTACCTAT GGCACCAACT TCAAACAGAA CAAGGCTTGG TAGATCAGTA   840
GAAGAAGATG GACAACTGCC ATGCCAGAGA CATCCACTCT ATGTAGACTT TGAAGAAATA   900
GGCTGGTCTG GATGGATCAT CTCTCCTAGA GGGTATAATG CTTACCACTG TAAAGGATCC   960
TGTCCATTTC CTTTGGGTCA GAACATGAGG CCTACAAACC ATGCCACTGT GCAGTCTATC  1020
ATCAATGCCC TCAAACTTAC AAAAGGTGTT AGTAGCCCGT GTTGTGTTCC TGACAAACTT  1080
TTCTCCATAA ATCTACTCTA CTTTGATGAT GATGAAAATG TTGTTTTGAA ACAGTATGAT  1140
GATATGGTCG CTGGCAGCTG CGGGTGCCAC                                  1170
```

( 2 ) INFORMATION FOR SEQ ID NO:2:

( i ) SEQUENCE CHARACTERISTICS:
        ( A ) LENGTH: 390 amino acids
        ( B ) TYPE: amino acids
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:2:

```
Met Asp Leu Arg Lys Met Leu Gly Phe Ile Phe Leu Phe Phe Ile Ile
  1               5                  10                  15
Gln Glu Cys Thr Ser Arg Pro Thr Asp Met Val Asp Ser Thr Asp Leu
             20                  25                  30
Glu Leu Glu Asp Pro Glu Leu Val Arg Ala Glu Ala Leu Lys Arg Leu
         35                  40                  45
Leu Glu Val Phe Gly Ile Glu Glu Pro Pro Gln Pro Leu Gln His Val
 50                  55                  60
Lys Gln Pro Pro Gln Tyr Met Val Asp Leu Tyr Asn Thr Val Ala Asp
 65                  70                  75                  80
Glu Asp Gly Val Thr Lys Asp Pro Asp Leu Leu Glu Gly Asn Thr Val
                 85                  90                  95
Arg Ser Phe Phe Asp Lys Ile His Ser Asp His Met His Phe Leu Phe
                100                 105                 110
Asn Leu Trp Thr Val Ala Arg Asn Glu Lys Ile Leu Thr Ala Glu Leu
            115                 120                 125
His Leu Phe Lys Leu Lys Pro Arg Pro Ser Glu Gln Ala Tyr Phe Lys
        130                 135                 140
Arg His His Phe Cys Gln Ile Ser Val Tyr Met Val Leu Asp Lys Asn
145                 150                 155                 160
Lys Ile Gln Leu Pro Gln Gly Arg Lys Leu Leu Ser Ser Lys Leu Val
                165                 170                 175
Pro Ile His Ser Ser Gly Trp Glu Val Phe Ser Ile Thr Gln Ala Val
            180                 185                 190
Arg Ala Trp Asn Asp Glu Ser Ala Asn His Gly Ile Leu Val Thr Val
        195                 200                 205
Arg Asn Leu Gly Gly Ala Gln Val Asp Pro Asn Ile Ile Arg Phe Ala
210                 215                 220
Ser Gly Arg Asp His His Glu Ser Lys Gln Pro Met Leu Val Leu Phe
225                 230                 235                 240
Thr Asp Asp Gly Arg Arg Gly Ile Val Ser Val Asn Asn Gln Pro Asp
                245                 250                 255
Asp Gln Leu Met Pro Leu Pro Asn Val Pro Met Ala Pro Thr Ser Asn
            260                 265                 270
Arg Thr Arg Leu Gly Arg Ser Val Glu Glu Asp Gly Gln Leu Pro Cys
        275                 280                 285
Gln Arg His Pro Leu Tyr Val Asp Phe Glu Glu Ile Gly Trp Ser Gly
        290                 295                 300
Trp Ile Ile Ser Pro Arg Gly Tyr Asn Ala Tyr His Cys Lys Gly Ser
305                 310                 315                 320
```

```
Cys Pro Phe Pro Leu Gly Gln Asn Met Arg Pro Thr Asn His Ala Thr
            325                     330                     335

Val Gln Ser Ile Ile Asn Ala Leu Lys Leu Thr Lys Gly Val Ser Ser
            340                 345                 350

Pro Cys Cys Val Pro Asp Lys Leu Phe Ser Ile Asn Leu Leu Tyr Phe
        355                 360                 365

Asp Asp Asp Glu Asn Val Val Leu Lys Gln Tyr Asp Asp Met Val Ala
    370                 375                 380

Gly Ser Cys Gly Cys His
385                 390
```

( 2 ) INFORMATION FOR SEQ ID NO:3:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( i x ) FEATURE:
        ( A ) NAME/KEY: Other
        ( B ) LOCATION: 6...6
        ( D ) OTHER INFORMATION: modified inosine ( x i ) SEQUENCE DESCRIPTION: SEQ ID NO:3:

ATHGGNTGGW SNGARTGGAT HAT                                           23

( 2 ) INFORMATION FOR SEQ ID NO:4:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( v ) FRAGMENT TYPE:

( v i ) ORIGINAL SOURCE:

( i x ) FEATURE:
        ( A ) NAME/KEY: Other
        ( B ) LOCATION: 3...3
        ( D ) OTHER INFORMATION: modified inosine ( x i ) SEQUENCE DESCRIPTION: SEQ ID NO:4:

ATNSW Y TGRA TNGTRGCRTG RTT                                      23

( 2 ) INFORMATION FOR SEQ ID NO:5:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:5:

ATGAGATGGA CCTTAGGAAG ATGTTGGGTT TTATATTTCT          40

(2) INFORMATION FOR SEQ ID NO:6:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:6:

GGAATTCTTA GTGGCACCCG CAGCTGCC          28

(2) INFORMATION FOR SEQ ID NO:7:

(i) SEQUENCE CHARACTERISTICS:
        (A) LENGTH: 2225 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:
        (A) ORGANISM: Xenopus genom (xi) SEQUENCE DESCRIPTION: SEQ ID NO:7:

```
TTCATTCACA AGAAACCTCG AGAGCTGCAG CTTGATGAG ATG GAC CTT AGG AAG      54
                                            Met Asp Leu Arg Lys
                                                              5

ATG TTG GGT TTT ATA TTT CTG TTT TTT ATC ATA CAA GAA TGT ACC TCC    102
Met Leu Gly Phe Ile Phe Leu Phe Phe Ile Ile Gln Glu Cys Thr Ser
              10              15                       20

AGA CCT ACT GAT ATG GTG GAC AGT ACT GAC CTT GAA TTA GAA GAC CCT    150
Arg Pro Thr Asp Met Val Asp Ser Thr Asp Leu Glu Leu Glu Asp Pro
            25              30              35

GAG CTA GTA AGA GCT GAA GCC CTG AAA AGA CTA TTG GAA GTG TTT GGT    198
Glu Leu Val Arg Ala Glu Ala Leu Lys Arg Leu Leu Glu Val Phe Gly
        40              45              50

ATT GAG GAA CCA CCA CAG CCT CTT CAG CAT GTC AAG CAG CCA CCT CAG    246
Ile Glu Glu Pro Pro Gln Pro Leu Gln His Val Lys Gln Pro Pro Gln
    55              60              65
```

```
TAT ATG GTG GAC CTT TAC AAC ACA GTA GCT GAT GAA GAT GGT GTA ACC        294
Tyr Met Val Asp Leu Tyr Asn Thr Val Ala Asp Glu Asp Gly Val Thr
70              75                  80                  85

AAG GAC CCA GAC CTT CTA GAA GGA AAT ACA GTC AGG AGT TTT TTT GAT        342
Lys Asp Pro Asp Leu Leu Glu Gly Asn Thr Val Arg Ser Phe Phe Asp
                    90                  95                  100

AAA ATT CAC AGC GAC CAT ATG CAT TTC TTG TTT AAC CTC TGG ACT GTG        390
Lys Ile His Ser Asp His Met His Phe Leu Phe Asn Leu Trp Thr Val
                105                 110                 115

GCC AGA AAC GAG AAG ATT CTA ACA GCA GAA CTT CAT CTT TTT AAA TTA        438
Ala Arg Asn Glu Lys Ile Leu Thr Ala Glu Leu His Leu Phe Lys Leu
        120                 125                 130

AAA CCA AGG CCT TCC GAG CAA GCT TAC TTC AAA AGG CAC CAC TTC TGC        486
Lys Pro Arg Pro Ser Glu Gln Ala Tyr Phe Lys Arg His His Phe Cys
135                 140                 145

CAG ATA AGT GTC TAT ATG GTC CTA GAT AAA AAT AAG ATA CAG TTG CCA        534
Gln Ile Ser Val Tyr Met Val Leu Asp Lys Asn Lys Ile Gln Leu Pro
150                 155                 160                 165

CAA GGA AGA AAA CTG CTA TCA TCA AAA CTT GTA CCA ATT CAT TCT TCA        582
Gln Gly Arg Lys Leu Leu Ser Ser Lys Leu Val Pro Ile His Ser Ser
                170                 175                 180

GGA TGG GAA GTG TTT TCT ATA ACC CAA GCT GTC CGA GCT TGG AAT GAT        630
Gly Trp Glu Val Phe Ser Ile Thr Gln Ala Val Arg Ala Trp Asn Asp
            185                 190                 195

GAA AGT GCT AAT CAT GGC ATC CTT GTA ACT GTC CGA AAT CTG GGA GGA        678
Glu Ser Ala Asn His Gly Ile Leu Val Thr Val Arg Asn Leu Gly Gly
        200                 205                 210

GCA CAA GTT GAT CCA AAC ATC ATC CGT TTT GCA TCT GGT AGA GAT CAC        726
Ala Gln Val Asp Pro Asn Ile Ile Arg Phe Ala Ser Gly Arg Asp His
215                 220                 225

CAT GAA AGC AAA CAG CCC ATG CTG GTT CTA TTC ACT GAT GAT GGA AGG        774
His Glu Ser Lys Gln Pro Met Leu Val Leu Phe Thr Asp Asp Gly Arg
230                 235                 240                 245

AGA GGA ATT GTC TCA GTA AAC AAT CAG CCT GAT GAC CAA TTA ATG CCC        822
Arg Gly Ile Val Ser Val Asn Asn Gln Pro Asp Asp Gln Leu Met Pro
                250                 255                 260

CTA CCA AAT GTA CCT ATG GCA CCA ACT TCA AAC AGA ACA AGG CTT GGT        870
Leu Pro Asn Val Pro Met Ala Pro Thr Ser Asn Arg Thr Arg Leu Gly
            265                 270                 275

AGA TCA GTA GAA GAA GAT GGA CAA CTG CCA TGC CAG AGA CAT CCA CTC        918
Arg Ser Val Glu Glu Asp Gly Gln Leu Pro Cys Gln Arg His Pro Leu
        280                 285                 290

TAT GTA GAC TTT GAA GAA ATA GGC TGG TCT GGA TGG ATC ATC TCT CCT        966
Tyr Val Asp Phe Glu Glu Ile Gly Trp Ser Gly Trp Ile Ile Ser Pro
295                 300                 305

AGA GGG TAT AAT GCT TAC CAC TGT AAA GGA TCC TGT CCA TTT CCT TTG       1014
Arg Gly Tyr Asn Ala Tyr His Cys Lys Gly Ser Cys Pro Phe Pro Leu
310                 315                 320                 325

GGT CAG AAC ATG AGG CCT ACA AAC CAT GCC ACT GTG CAG TCT ATC ATC       1062
Gly Gln Asn Met Arg Pro Thr Asn His Ala Thr Val Gln Ser Ile Ile
                330                 335                 340

AAT GCC CTC AAA CTT ACA AAA GGT GTT AGT AGC CCG TGT TGT GTT CCT       1110
Asn Ala Leu Lys Leu Thr Lys Gly Val Ser Ser Pro Cys Cys Val Pro
            345                 350                 355

GAC AAA CTT TTC TCC ATA AAT CTA CTC TAC TTT GAT GAT GAT GAA AAT       1158
Asp Lys Leu Phe Ser Ile Asn Leu Leu Tyr Phe Asp Asp Asp Glu Asn
        360                 365                 370

GTT GTT TTG AAA CAG TAT GAT GAT ATG GTC GCT GGC AGC TGC GGG TGC       1206
Val Val Leu Lys Gln Tyr Asp Asp Met Val Ala Gly Ser Cys Gly Cys
375                 380                 385
```

| CAC | TAAAAACATT | TTGGTCACAC | ACCTACAAAT | GGTGGTACTG | TCTAAGGTGC | 1259 |
|---|---|---|---|---|---|---|
| His | | | | | | |

390

| AAACTAGGGA | AACCCATAGA | AACAGACCCC | ATGTTTGGTG | AAATTCTAAA | AGCACTGTAT | 1319 |
|---|---|---|---|---|---|---|
| TTTCAGTTGT | TCTGCAACTG | AGAGTTTCTG | AGAACTGGAC | TGTTAATGTT | ATGCTTTATA | 1379 |
| GATCAATAAG | GCCAGTCATT | TCGGTTTTAG | TTTTCAAAAT | ATGATTACAA | GTCTATAAAG | 1439 |
| GACTGTATCT | ATAACATGTA | AATACTGGAG | ATAGTATTAA | ACGATCATAT | TGTTTCAGTC | 1499 |
| AGTATCTATA | GAAATACTG | ATATCTAACT | GCAACAATAA | AATACAACCT | AGTATCTCAT | 1559 |
| GTATACTGTC | TGAAAGGGAT | GATAAGAATT | GGAATGTCCA | CCTCCTTATG | CATAGATTAC | 1619 |
| TGTTAATGTT | ACTTCAGAAA | GTATCATTTA | TAGCCACCAT | GTGGCTCTGT | GAGTTGTAAT | 1679 |
| GCAGTACACC | ACAAATCCGG | CAGGTAATAA | CTTATTTTGT | AAATTGTTTT | CCTAAACATA | 1739 |
| TATTTTATAG | GCAGCTTGTG | CACTGGCATT | TTAAGATTCA | CCCATTGTCC | ATTGCACCAT | 1799 |
| GGTTAAACTG | TTTTTTTATC | CCTAACCTAG | TGGGATGTAT | AGAAATTACA | GAGCATATCA | 1859 |
| ATTAATTGCA | GGTAGGTACA | GCAATAAAGC | AATACCTAGT | ACCTAGCGAA | ACTAGAATTG | 1919 |
| AACTAGAATT | GAATATTTCT | TTCTGCCATG | GTGTTTCTT | GCTTAACGT | TTGTCCACAG | 1979 |
| CAAAATTATC | TGTTTGCTCT | TTTGATATTC | TTTTATTATA | CAAAAATACA | TTAAAGGGTG | 2039 |
| GTTATGTTTT | AATGATGTCA | GTGCTCATGT | GGCTTTAAAC | AAAACTTGCC | TGTACTGCTT | 2099 |
| ATTACTCTTT | GTAATATTTG | TATATAAGTA | AATTGTTAAT | ATATAATGCT | TGCATTGTAA | 2159 |
| ATCTGTAAAC | TTAATGTGTG | AGGTTCCTTT | TTCTTTTAAA | AATGTACATA | TTAAAATATA | 2219 |
| TGCATT | | | | | | 2225 |

( 2 ) INFORMATION FOR SEQ ID NO:8:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x ) PUBLICATION INFORMATION:
        ( A ) AUTHORS: NIEHRS, C.
            STEINBEISSER, H.
            DE ROBERTIS, E. M.
        ( B ) TITLE: MESODERMAL PATTERNING BY A GRADIENT OF
            THE VERTEBRATE HOMEOBOX GENE GOOSECOID
        ( C ) JOURNAL: SCIENCE
        ( D ) VOLUME:
        ( E ) ISSUE: 263 (1994)
        ( F ) PAGES: 817-820

( x i ) SEQUENCE DESCRIPTION: SEQ ID NO:8:

| GCTGGAAGTA | TGTGAATGGA | GA | 22 |
|---|---|---|---|

( 2 ) INFORMATION FOR SEQ ID NO:9:

( i ) SEQUENCE CHARACTERISTICS:
        ( A ) LENGTH: 22 base pairs
        ( B ) TYPE: nucleic acid
        ( C ) STRANDEDNESS: single (D) TOPOLOGY: linear (ii) MOLECULE TYPE: cDNA (iii) HYPOTHETICAL: NO (iv) ANTI-SENSE: YES (v) FRAGMENT TYPE:

(vi) ORIGINAL SOURCE:

(x) PUBLICATION INFORMATION:
       (A) AUTHORS: NIEHRS, C.
                    STEINBEISSER, H.
                    DE ROBERTIS, E. M.
       (B) TITLE: MESODERMAL PATTERNING BY A GRADIENT OF
                  THE VERTEBRATE HOMEOBOX GENE GOOSECOID
       (C) JOURNAL: SCIENCE
       (D) VOLUME:
       (E) ISSUE: 263 (1994)
       (F) PAGES: 817-820

(xi) SEQUENCE DESCRIPTION: SEQ ID NO:9:

TTTAAGTGCT GTAATCTCTT CA                                                    22

(2) INFORMATION FOR SEQ ID NO:10:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(vii) IMMEDIATE SOURCE:
       (A) LIBRARY: GENEWORKS, M27730

(xi) SEQUENCE DESCRIPTION: SEQ ID NO:10:

AGTCCGATCT CAGTGAAGCG                                                       20

(2) INFORMATION FOR SEQ ID NO:11:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: cDNA (iii) HYPOTHETICAL: NO (iv) ANTI-SENSE: YES (v) FRAGMENT TYPE:

(vi) ORIGINAL SOURCE:

(vii) IMMEDIATE SOURCE:
       (A) LIBRARY: GENEWORKS, M27730

(xi) SEQUENCE DESCRIPTION: SEQ ID NO:11:

AGTCGATGTA TCTGGAGGCC                                                       20

( 2 ) INFORMATION FOR SEQ ID NO:12:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( v i i ) IMMEDIATE SOURCE:
        ( A ) LIBRARY: GENEWORKS, D10455

( x i ) SEQUENCE DESCRIPTION: SEQ ID NO:12:

```
CTCGCATGTC TTAGTACCTC AACCAAC                                    27
```

( 2 ) INFORMATION FOR SEQ ID NO:13:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( v ) FRAGMENT TYPE:

( v i ) ORIGINAL SOURCE:

( v i i ) IMMEDIATE SOURCE:
        ( A ) LIBRARY: GENEWORKS, D10455

( x i ) SEQUENCE DESCRIPTION: SEQ ID NO:13:

```
GTCATATCTT CCCTCTG                                               17
```

( 2 ) INFORMATION FOR SEQ ID NO:14:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x ) PUBLICATION INFORMATION:
        ( A ) AUTHORS: RUPP, R. A.
                      WEINTRAUB, H.
        ( B ) TITLE: UBIQUITOUS MYOD TRANSCRIPTION AT THE MIDBLASTULA
              TRANSITION PRECEDS INDUCTION-DEPENDENT MYOD
              EXPRESSION IN PRESUMPTIVE MESODERM OF X. LAEVIS
        ( C ) JOURNAL: CELL
        ( D ) VOLUME:
        ( E ) ISSUE: 65 (1991)
        ( F ) PAGES: 927-937

( x i ) SEQUENCE DESCRIPTION: SEQ ID NO:14:

AGCTCCAACT GCTCCGACGG CATGAA                                                                26

( 2 ) INFORMATION FOR SEQ ID NO:15:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( v ) FRAGMENT TYPE:

( v i ) ORIGINAL SOURCE:

( x ) PUBLICATION INFORMATION:
        ( A ) AUTHORS: RUPP, R. A.
                    WEINTRAUB, H.
        ( B ) TITLE: UBIQUITOUS MYOD TRANSCRIPTION AT THE MIDBLASTULA
             TRANSITION PRECEDS INDUCTION-DEPENDENT MYOD
             EXPRESSION IN PRESUMPTIVE MESODERM OF X. LAEVIS
        ( C ) JOURNAL: CELL
        ( D ) VOLUME:
        ( E ) ISSUE: 65 (1991)
        ( F ) PAGES: 927-937

( x i ) SEQUENCE DESCRIPTION: SEQ ID NO:15:

AGGAGAGAAT CCAGTTGATG GAAACA                                                                26

( 2 ) INFORMATION FOR SEQ ID NO:16:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x ) PUBLICATION INFORMATION:
        ( A ) AUTHORS: RUPP, R. A.
                    WEINTRAUB, H.
        ( B ) TITLE: UBIQUITOUS MYOD TRANSCRIPTION AT THE MIDBLASTULA
             TRANSITION PRECEDS INDUCTION-DEPENDENT MYOD
             EXPRESSION IN PRESUMPTIVE MESODERM OF X. LAEVIS
        ( C ) JOURNAL: CELL
        ( D ) VOLUME:
        ( E ) ISSUE: 65 (1991)
        ( F ) PAGES: 927-937

( x i ) SEQUENCE DESCRIPTION: SEQ ID NO:16:

AACTGCTCCG ATGGCATGAT GGATTA                                                                26

( 2 ) INFORMATION FOR SEQ ID NO:17:

( i ) SEQUENCE CHARACTERISTICS:
        ( A ) LENGTH: 26 base pairs
        ( B ) TYPE: nucleic acid
        ( C ) STRANDEDNESS: single (D) TOPOLOGY: linear (ii) MOLECULE TYPE: cDNA (iii) HYPOTHETICAL: NO (iv) ANTI-SENSE: YES (v) FRAGMENT TYPE:

(vi) ORIGINAL SOURCE:

(x) PUBLICATION INFORMATION:
 (A) AUTHORS: RUPP, R. A.
   WEINTRAUB, H.
 (B) TITLE: UBIQUITOUS MYOD TRANSCRIPTION AT THE MIDBLASTULA
   TRANSITION PRECEDS INDUCTION-DEPENDENT MYOD
   EXPRESSION IN PRESUMPTIVE MESODERM OF X. LAEVIS
 (C) JOURNAL: CELL
 (D) VOLUME:
 (E) ISSUE: 65 (1991)
 (F) PAGES: 927-937

(xi) SEQUENCE DESCRIPTION: SEQ ID NO:17:

ATTGCTGGGA GAAGGGATGG TGATTA                    26

(2) INFORMATION FOR SEQ ID NO:18:

(i) SEQUENCE CHARACTERISTICS:
 (A) LENGTH: 19 base pairs
 (B) TYPE: nucleic acid
 (C) STRANDEDNESS: single
 (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(vii) IMMEDIATE SOURCE:
 (A) LIBRARY: GENEWORKS, M88594

(xi) SEQUENCE DESCRIPTION: SEQ ID NO:18:

TGTTGCGAAT AATCGGAGC                        19

(2) INFORMATION FOR SEQ ID NO:19:

(i) SEQUENCE CHARACTERISTICS:
 (A) LENGTH: 20 base pairs
 (B) TYPE: nucleic acid
 (C) STRANDEDNESS: single
 (D) TOPOLOGY: linear (ii) MOLECULE TYPE: cDNA (iii) HYPOTHETICAL: NO (iv) ANTI-SENSE: YES (v) FRAGMENT TYPE:

(vi) ORIGINAL SOURCE:

(vii) IMMEDIATE SOURCE:
 (A) LIBRARY: GENEWORKS, M88594

(xi) SEQUENCE DESCRIPTION: SEQ ID NO:19:

TTATGTCCAG CAACTGCAGC                       20

( 2 ) INFORMATION FOR SEQ ID NO:20:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( v i i ) IMMEDIATE SOURCE:
        ( A ) LIBRARY: GENEWORKS, X57234

( x i ) SEQUENCE DESCRIPTION: SEQ ID NO:20:

ATGGACTTCG AAGTGCAACC         20

( 2 ) INFORMATION FOR SEQ ID NO:21:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( v ) FRAGMENT TYPE:

( v i ) ORIGINAL SOURCE:

( v i i ) IMMEDIATE SOURCE:
        ( A ) LIBRARY: GENEWORKS, X57234

( x i ) SEQUENCE DESCRIPTION: SEQ ID NO:21:

ATGGCTCCTC TGTTGTCAGC         20

( 2 ) INFORMATION FOR SEQ ID NO:22:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( v i i ) IMMEDIATE SOURCE:
        ( A ) LIBRARY: GENEWORKS, M98807

( x i ) SEQUENCE DESCRIPTION: SEQ ID NO:22:

CTAAGTAGCC AGAGGGACGA G         21

( 2 ) INFORMATION FOR SEQ ID NO:23:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( i i ) MOLECULE TYPE: cDNA ( i i i ) HYPOTHETICAL: NO ( i v ) ANTI-SENSE: YES ( v ) FRAGMENT TYPE:

( v i ) ORIGINAL SOURCE:

( v i i ) IMMEDIATE SOURCE:
  ( A ) LIBRARY: GENEWORKS, M98807

( x i ) SEQUENCE DESCRIPTION: SEQ ID NO:23:

ACACAGCTGC ACAAATAAG     20

( 2 ) INFORMATION FOR SEQ ID NO:24:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x ) PUBLICATION INFORMATION:
    ( A ) AUTHORS: NIEHRS, C.
       STEINBEISSER, H.
       DE ROBERTIS, E. M.
    ( B ) TITLE: MESODERMAL PATTERNING BY A GRADIENT OF
       THE VERTEBRATE HOMEOBOX GENE GOOSECOID
    ( C ) JOURNAL: SCIENCE
    ( D ) VOLUME:
    ( E ) ISSUE: 263 (1994)
    ( F ) PAGES: 817-820

( x i ) SEQUENCE DESCRIPTION: SEQ ID NO:24:

AGATTACAGC GGATTTTA     18

( 2 ) INFORMATION FOR SEQ ID NO:25:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: YES ( v ) FRAGMENT TYPE:

( v i ) ORIGINAL SOURCE:

( x ) PUBLICATION INFORMATION:
    ( A ) AUTHORS: NIEHRS, C.
       STEINBEISSER, H.
       DE ROBERTIS, E. M.

(B) TITLE: MESODERMAL PATTERNING BY A GRADIENT OF
THE VERTEBRATE HOMEOBOX GENE GOOSECOID
(C) JOURNAL: SCIENCE
(D) VOLUME:
(E) ISSUE: 263 (1994)
(F) PAGES: 817-820

(x i) SEQUENCE DESCRIPTION: SEQ ID NO:25:

CTGGGTACTT GGTTTCT　　　　　　　　　　　　　　　　　　　　　　　　　　　17

(2) INFORMATION FOR SEQ ID NO:26:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(x i) SEQUENCE DESCRIPTION: SEQ ID NO:26:

TATTGAGGAA CCACCACAGC　　　　　　　　　　　　　　　　　　　　　　　　　　20

(2) INFORMATION FOR SEQ ID NO:27:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (v) FRAGMENT TYPE:

(vi) ORIGINAL SOURCE:

(x i) SEQUENCE DESCRIPTION: SEQ ID NO:27:

CTTATCTGGC AGAAGTGGTG C　　　　　　　　　　　　　　　　　　　　　　　　21

(2) INFORMATION FOR SEQ ID NO:28:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(x i) SEQUENCE DESCRIPTION: SEQ ID NO:28:

GAGCTGCAGC TTGATGAG　　　　　　　　　　　　　　　　　　　　　　　　　　18

( 2 ) INFORMATION FOR SEQ ID NO:29:

( i ) SEQUENCE CHARACTERISTICS:
       ( A ) LENGTH: 18 base pairs
       ( B ) TYPE: nucleic acid
       ( C ) STRANDEDNESS: single
       ( D ) TOPOLOGY: linear ( i i ) MOLECULE TYPE: cDNA ( i i i ) HYPOTHETICAL: NO ( i v ) ANTI-SENSE: YES ( v ) FRAGMENT TYPE:

( v i ) ORIGINAL SOURCE:

( x i ) SEQUENCE DESCRIPTION: SEQ ID NO:29:

GCCACAGTCC AGAGGTTA                                                                                              18

( 2 ) INFORMATION FOR SEQ ID NO:30:

( i ) SEQUENCE CHARACTERISTICS:
       ( A ) LENGTH: 21 base pairs
       ( B ) TYPE: nucleic acid
       ( C ) STRANDEDNESS: single
       ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x ) PUBLICATION INFORMATION:
       ( A ) AUTHORS: HEMMATI-BRIVANLOU, A.
                      KELLY, O. G.
                      MELTON, D. A.
       ( B ) TITLE: FOLLISTATIN, AN ANTAGONIST OF ACTIVIN, IS
                    EXPRESSED IN THE SPEMANN ORGANIZER AND
                    DISPLAYS DIRECT NEURALIZING ACTIVITY
       ( C ) JOURNAL: CELL
       ( D ) VOLUME:
       ( E ) ISSUE: 77 (1994)
       ( F ) PAGES: 283-295

( x i ) SEQUENCE DESCRIPTION: SEQ ID NO:30:

CAATAGAGTC CGGACTTGTG C                                                                                          21

( 2 ) INFORMATION FOR SEQ ID NO:31:

( i ) SEQUENCE CHARACTERISTICS:
       ( A ) LENGTH: 20 base pairs
       ( B ) TYPE: nucleic acid
       ( C ) STRANDEDNESS: single
       ( D ) TOPOLOGY: linear ( i i ) MOLECULE TYPE: cDNA ( i i i ) HYPOTHETICAL: NO ( i v ) ANTI-SENSE: YES ( v ) FRAGMENT TYPE:

( v i ) ORIGINAL SOURCE:

( x ) PUBLICATION INFORMATION:
       ( A ) AUTHORS: HEMMATI-BRIVANLOU, A.
                      KELLY, O. G.

MELTON, D. A.
        ( B ) TITLE: FOLLISTATIN, AN ANTAGONIST OF ACTIVIN, IS
              EXPRESSED IN THE SPEMANN ORGANIZER AND
              DISPLAYS DIRECT NEURALIZING ACTIVITY
        ( C ) JOURNAL: CELL
        ( D ) VOLUME:
        ( E ) ISSUE: 77 (1994)
        ( F ) PAGES: 283-295

( x i ) SEQUENCE DESCRIPTION: SEQ ID NO:31:

TACAGAACCT GACATCGGCC					20

( 2 ) INFORMATION FOR SEQ ID NO:32:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x ) PUBLICATION INFORMATION:
        ( A ) AUTHORS: HEMMATI-BRIVANLOU, A.
              MELTON, D. A.
        ( B ) TITLE: INHIBITION OF ACTIVIN RECEPTOR SIGNALING
              PROMOTES NEURALIZATION IN XENOPUS
        ( C ) JOURNAL: CELL
        ( D ) VOLUME:
        ( E ) ISSUE: 77 (1994)
        ( F ) PAGES: 273-281

( x i ) SEQUENCE DESCRIPTION: SEQ ID NO:32:

CACAGTTCCA CCAAATGC					18

( 2 ) INFORMATION FOR SEQ ID NO:33:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( v ) FRAGMENT TYPE:

( v i ) ORIGINAL SOURCE:

( x ) PUBLICATION INFORMATION:
        ( A ) AUTHORS: HEMMATI-BRIVANLOU, A.
              MELTON, D. A.
        ( B ) TITLE: INHIBITION OF ACTIVIN RECEPTOR SIGNALING
              PROMOTES NEURALIZATION IN XENOPUS
        ( C ) JOURNAL: CELL
        ( D ) VOLUME:
        ( E ) ISSUE: 77 (1994)
        ( F ) PAGES: 273-281

( x i ) SEQUENCE DESCRIPTION: SEQ ID NO:33:

GGAATCAAGC GGTACAGA					18

( 2 ) INFORMATION FOR SEQ ID NO:34:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x ) PUBLICATION INFORMATION:
        ( A ) AUTHORS: HEMMATI-BRIVANLOU, A.
            MELTON, D. A.
        ( B ) TITLE: INHIBITION OF ACTIVIN RECEPTOR SIGNALING
            PROMOTES NEURALIZATION IN XENOPUS
        ( C ) JOURNAL: CELL
        ( D ) VOLUME:
        ( E ) ISSUE: 77 (1994)
        ( F ) PAGES: 273-281

( x i ) SEQUENCE DESCRIPTION: SEQ ID NO:34:

GCTGACAGAA TGCAGAAG                                                          18

( 2 ) INFORMATION FOR SEQ ID NO:35:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( v ) FRAGMENT TYPE:

( v i ) ORIGINAL SOURCE:

( x ) PUBLICATION INFORMATION:
        ( A ) AUTHORS: HEMMATI-BRIVANLOU, A.
            MELTON, D. A.
        ( B ) TITLE: INHIBITION OF ACTIVIN RECEPTOR SIGNALING
            PROMOTES NEURALIZATION IN XENOPUS
        ( C ) JOURNAL: CELL
        ( D ) VOLUME:
        ( E ) ISSUE: 77 (1994)
        ( F ) PAGES: 273-281

( x i ) SEQUENCE DESCRIPTION: SEQ ID NO:35:

TTGCTTGGAG GAGTGTGT                                                          18

( 2 ) INFORMATION FOR SEQ ID NO:36:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO (v) FRAGMENT TYPE:

(vi) ORIGINAL SOURCE:

(x) PUBLICATION INFORMATION:
    (A) AUTHORS: NIEHRS, C.
              STEINBEISSER, H.
              DE ROBERTIS, E. M.
    (B) TITLE: MESODERMAL PATTERNING BY A GRADIENT OF
          THE VERTEBRATE HOMEOBOX GENE GOOSECOID
    (C) JOURNAL: SCIENCE
    (D) VOLUME:
    (E) ISSUE: 263 (1994)
    (F) PAGES: 817-820

(xi) SEQUENCE DESCRIPTION: SEQ ID NO:36:

TCCCTGTACG CTTCTGGTCG TA                    22

(2) INFORMATION FOR SEQ ID NO:37:

(i) SEQUENCE CHARACTERISTICS:
    (A) LENGTH: 22 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: YES (v) FRAGMENT TYPE:

(vi) ORIGINAL SOURCE:

(x) PUBLICATION INFORMATION:
    (A) AUTHORS: NIEHRS, C.
              STEINBEISSER, H.
              DE ROBERTIS, E. M.
    (B) TITLE: MESODERMAL PATTERNING BY A GRADIENT OF
          THE VERTEBRATE HOMEOBOX GENE GOOSECOID
    (C) JOURNAL: SCIENCE
    (D) VOLUME:
    (E) ISSUE: 263 (1994)
    (F) PAGES: 817-820

(xi) SEQUENCE DESCRIPTION: SEQ ID NO:37:

TCTCAAAGTC CAAAGCCACA TA                    22

(2) INFORMATION FOR SEQ ID NO:38:

(i) SEQUENCE CHARACTERISTICS:
    (A) LENGTH: 24 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(x) PUBLICATION INFORMATION:
    (A) AUTHORS: NIEHRS, C.
              STEINBEISSER, H.
              DE ROBERTIS, E. M.
    (B) TITLE: MESODERMAL PATTERNING BY A GRADIENT OF
          THE VERTEBRATE HOMEOBOX GENE GOOSECOID
    (C) JOURNAL: SCIENCE
    (D) VOLUME:

(E) ISSUE: 263 (1994)
        (F) PAGES: 817-820

(x i) SEQUENCE DESCRIPTION: SEQ ID NO:38:

CGGGATAACA TTCAGGGTAT CACT                                                                           24

(2) INFORMATION FOR SEQ ID NO:39:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO (i v) ANTI-SENSE: YES (v) FRAGMENT TYPE:

(v i) ORIGINAL SOURCE:

(x) PUBLICATION INFORMATION:
        (A) AUTHORS: NIEHRS, C.
                     STEINBEISSER, H.
                     DE ROBERTIS, E. M.
        (B) TITLE: MESODERMAL PATTERNING BY A GRADIENT OF
                   THE VERTEBRATE HOMEOBOX GENE GOOSECOID
        (C) JOURNAL: SCIENCE
        (D) VOLUME:
        (E) ISSUE: 263 (1994)
        (F) PAGES: 817-820

(x i) SEQUENCE DESCRIPTION: SEQ ID NO:39:

ATCCATGGCG GTAACTGTCT TCCT                                                                           24

(2) INFORMATION FOR SEQ ID NO:40:

(i) SEQUENCE CHARACTERISTICS:
        (A) LENGTH: 103 amino acids
        (B) TYPE: amino acids
        (C) STRANDEDNESS: single
        (D) TOPOLOGY: linear (i i) MOLECULE TYPE: peptide (i i i) HYPOTHETICAL: NO (i v) ANTI-SENSE: NO (v) FRAGMENT TYPE: C-terminal (v i) ORIGINAL SOURCE:

(x i) SEQUENCE DESCRIPTION: SEQ ID NO:40:

| Cys | Gln | Arg | His | Pro | Leu | Tyr | Val | Asp | Phe | Glu | Glu | Ile | Gly | Trp | Ser |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Gly | Trp | Ile | Ile | Ser | Pro | Arg | Gly | Tyr | Asn | Ala | Tyr | His | Cys | Lys | Gly |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Ser | Cys | Pro | Phe | Pro | Leu | Gly | Gln | Asn | Met | Arg | Pro | Thr | Asn | His | Ala |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Thr | Val | Gln | Ser | Ile | Ile | Asn | Ala | Leu | Lys | Leu | Thr | Lys | Gly | Val | Ser |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Ser | Pro | Cys | Cys | Val | Pro | Asp | Lys | Leu | Phe | Ser | Ile | Asn | Leu | Leu | Tyr |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Phe | Asp | Asp | Asp | Glu | Asn | Val | Val | Leu | Lys | Gln | Tyr | Asp | Asp | Met | Val |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

```
Ala  Gly  Ser  Cys  Gly  Cys  His
              100
```

( 2 ) INFORMATION FOR SEQ ID NO:41:

( i ) SEQUENCE CHARACTERISTICS:
        ( A ) LENGTH: 103 amino acids
        ( B ) TYPE: amino acids
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: C-terminal ( v i ) ORIGINAL SOURCE:

( x i ) SEQUENCE DESCRIPTION: SEQ ID NO:41:

```
Cys  Ala  Arg  Arg  Tyr  Leu  Lys  Val  Asp  Phe  Ala  Asp  Ile  Gly  Trp  Ser
 1                  5                       10                      15
Glu  Trp  Ile  Ile  Ser  Pro  Lys  Ser  Phe  Asp  Ala  Tyr  Tyr  Cys  Ser  Gly
              20                       25                      30
Ala  Cys  Gln  Phe  Pro  Met  Pro  Lys  Ser  Leu  Lys  Pro  Ser  Asn  His  Ala
         35                       40                      45
Thr  Ile  Gln  Ser  Ile  Val  Arg  Ala  Val  Gly  Val  Val  Pro  Gly  Ile  Pro
    50                       55                      60
Glu  Pro  Cys  Cys  Val  Pro  Glu  Lys  Met  Ser  Ser  Leu  Ser  Ile  Leu  Phe
65                       70                      75                      80
Phe  Asp  Glu  Asn  Lys  Asn  Val  Val  Leu  Lys  Val  Tyr  Pro  Asn  Met  Thr
                   85                      90                      95
Val  Glu  Ser  Cys  Ala  Cys  Arg
              100
```

( 2 ) INFORMATION FOR SEQ ID NO:42:

( i ) SEQUENCE CHARACTERISTICS:
        ( A ) LENGTH: 101 amino acids
        ( B ) TYPE: amino acids
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: C-terminal ( v i ) ORIGINAL SOURCE:

( x i ) SEQUENCE DESCRIPTION: SEQ ID NO:42:

```
Cys  Lys  Arg  His  Pro  Leu  Tyr  Val  Asp  Phe  Ser  Asp  Val  Gly  Trp  Asn
 1                  5                       10                      15
Asp  Trp  Ile  Val  Ala  Pro  Pro  Gly  Tyr  His  Ala  Phe  Tyr  Cys  His  Gly
              20                       25                      30
Glu  Cys  Pro  Phe  Pro  Leu  Ala  Asp  His  Leu  Asn  Ser  Thr  Asn  His  Ala
         35                       40                      45
Ile  Val  Gln  Thr  Leu  Val  Asn  Ser  Val  Asn  Ser  Lys  Ile  Pro  Lys  Ala
    50                       55                      60
Cys  Cys  Val  Pro  Thr  Glu  Leu  Ser  Ala  Ile  Ser  Met  Leu  Tyr  Leu  Asp
65                       70                      75                      80
```

```
Glu  Asn  Glu  Lys  Val  Val  Leu  Lys  Asn  Tyr  Gln  Asp  Met  Val  Val  Glu
               85                      90                            95
Gly  Cys  Gly  Cys  Arg
                100
```

( 2 ) INFORMATION FOR SEQ ID NO:43:

( i ) SEQUENCE CHARACTERISTICS:
        ( A ) LENGTH: 101 amino acids
        ( B ) TYPE: amino acids
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: C-terminal ( v i ) ORIGINAL SOURCE:

( x i ) SEQUENCE DESCRIPTION: SEQ ID NO:43:

```
Cys  Arg  Arg  His  Ser  Leu  Tyr  Val  Asp  Phe  Ser  Asp  Val  Gly  Trp  Asn
 1                    5                      10                           15
Asp  Trp  Ile  Val  Ala  Pro  Pro  Gly  Tyr  Gln  Ala  Phe  Tyr  Cys  His  Gly
               20                      25                      30
Asp  Cys  Pro  Phe  Pro  Leu  Ala  Asp  His  Leu  Asn  Ser  Thr  Asn  His  Ala
          35                      40                      45
Ile  Val  Gln  Thr  Leu  Val  Asn  Ser  Val  Asn  Ser  Ser  Ile  Pro  Lys  Ala
          50                   55                      60
Cys  Cys  Val  Pro  Thr  Glu  Leu  Ser  Ala  Ile  Ser  Met  Leu  Tyr  Leu  Asp
 65                      70                      75                           80
Glu  Tyr  Asp  Lys  Val  Val  Leu  Lys  Asn  Tyr  Gln  Glu  Met  Val  Val  Glu
               85                      90                            95
Gly  Cys  Gly  Cys  Arg
                100
```

( 2 ) INFORMATION FOR SEQ ID NO:44:

( i ) SEQUENCE CHARACTERISTICS:
        ( A ) LENGTH: 102 amino acids
        ( B ) TYPE: amino acids
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: C-terminal ( v i ) ORIGINAL SOURCE:

( x i ) SEQUENCE DESCRIPTION: SEQ ID NO:44:

```
Cys  Lys  Lys  Arg  His  Leu  Tyr  Val  Glu  Phe  Lys  Asp  Val  Gly  Trp  Gln
 1                    5                      10                           15
Asn  Trp  Val  Ile  Ala  Pro  Gln  Gly  Tyr  Met  Ala  Asn  Tyr  Cys  Tyr  Gly
               20                      25                      30
Glu  Cys  Pro  Tyr  Pro  Leu  Thr  Glu  Ile  Leu  Asn  Gly  Ser  Asn  His  Ala
          35                      40                      45
Ile  Leu  Gln  Thr  Leu  Val  His  Ser  Ile  Glu  Pro  Glu  Asp  Ile  Pro  Leu
```

-continued

```
            50                         55                          60
Pro  Cys  Cys  Val  Pro  Thr  Lys  Met  Ser  Pro  Ile  Ser  Met  Leu  Phe  Tyr
65                       70                       75                           80

Asp  Asn  Asn  Asp  Asn  Val  Val  Leu  Arg  His  Tyr  Glu  Asn  Met  Ala  Val
                    85                      90                       95

Asp  Glu  Cys  Gly  Cys  Arg
                    100
```

( 2 ) INFORMATION FOR SEQ ID NO:45:

( i ) SEQUENCE CHARACTERISTICS:
        ( A ) LENGTH: 106 amino acids
        ( B ) TYPE: amino acids
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: C-terminal ( v i ) ORIGINAL SOURCE:

( x i ) SEQUENCE DESCRIPTION: SEQ ID NO:45:

```
Cys  Arg  Ala  Arg  Arg  Leu  Tyr  Val  Ser  Phe  Arg  Glu  Val  Gly  Trp  His
1                   5                     10                      15

Arg  Trp  Val  Ile  Ala  Pro  Arg  Gly  Phe  Leu  Ala  Asn  Tyr  Cys  Gln  Gly
                    20                    25                      30

Gln  Cys  Ala  Leu  Pro  Val  Ala  Leu  Ser  Gly  Ser  Gly  Gly  Pro  Pro  Ala
                35                        40                      45

Leu  Asn  His  Ala  Val  Leu  Arg  Ala  Leu  Met  His  Ala  Ala  Ala  Pro  Gly
     50                       55                      60

Ala  Ala  Asp  Leu  Pro  Cys  Cys  Val  Pro  Ala  Arg  Leu  Ser  Pro  Ile  Ser
65                       70                       75                           80

Val  Leu  Phe  Phe  Asp  Asn  Ser  Asp  Asn  Val  Val  Leu  Arg  Gln  Tyr  Glu
                    85                      90                       95

Asp  Met  Val  Val  Asp  Glu  Cys  Gly  Cys  Arg
                    100                     105
```

( 2 ) INFORMATION FOR SEQ ID NO:46:

( i ) SEQUENCE CHARACTERISTICS:
        ( A ) LENGTH: 103 amino acids
        ( B ) TYPE: amino acids
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: C-terminal ( v i ) ORIGINAL SOURCE:

( x i ) SEQUENCE DESCRIPTION: SEQ ID NO:46:

```
Cys  Lys  Lys  His  Glu  Leu  Tyr  Val  Ser  Phe  Arg  Asp  Leu  Gly  Trp  Gln
1                   5                     10                      15

Asp  Trp  Ile  Ile  Ala  Pro  Glu  Gly  Tyr  Ala  Ala  Phe  Tyr  Cys  Asp  Gly
                    20                    25                      30
```

```
Glu  Cys  Ser  Phe  Pro  Leu  Asn  Ala  His  Met  Asn  Ala  Thr  Asn  His  Ala
          35                       40                      45

Ile  Val  Gln  Thr  Leu  Val  His  Leu  Met  Phe  Pro  Asp  His  Val  Pro  Lys
          50                  55                      60

Pro  Cys  Cys  Ala  Pro  Thr  Lys  Leu  Asn  Ala  Ile  Ser  Val  Leu  Tyr  Phe
65                       70                      75                           80

Asp  Asp  Ser  Ser  Asn  Val  Ile  Leu  Lys  Lys  Tyr  Arg  Asn  Met  Val  Val
               85                       90                           95

Arg  Ser  Cys  Gly  Cys  His  Ile
                100
```

(2) INFORMATION FOR SEQ ID NO:47:

(i) SEQUENCE CHARACTERISTICS:
        (A) LENGTH: 102 amino acids
        (B) TYPE: amino acids
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: C-terminal (vi) ORIGINAL SOURCE:

(xi) SEQUENCE DESCRIPTION: SEQ ID NO:47:

```
Cys  Lys  Lys  His  Glu  Leu  Tyr  Val  Ser  Phe  Arg  Asp  Leu  Gly  Trp  Gln
 1                   5                        10                          15

Asp  Trp  Ile  Ile  Ala  Pro  Glu  Gly  Tyr  Ala  Ala  Tyr  Tyr  Cys  Glu  Gly
               20                       25                           30

Glu  Cys  Ala  Phe  Pro  Leu  Asn  Ser  Tyr  Met  Asn  Ala  Thr  Asn  His  Ala
          35                       40                      45

Ile  Val  Gln  Thr  Leu  Val  His  Phe  Ile  Asn  Pro  Glu  Thr  Val  Pro  Lys
          50                  55                      60

Pro  Cys  Cys  Ala  Pro  Thr  Gln  Leu  Asn  Ala  Ile  Ser  Val  Leu  Tyr  Phe
65                       70                      75                           80

Asp  Asp  Ser  Ser  Asn  Val  Ile  Leu  Lys  Lys  Tyr  Arg  Asn  Met  Val  Val
               85                       90                           95

Arg  Ala  Cys  Gly  Cys  His
                100
```

(2) INFORMATION FOR SEQ ID NO:48:

(i) SEQUENCE CHARACTERISTICS:
        (A) LENGTH: 103 amino acids
        (B) TYPE: amino acids
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: C-terminal (vi) ORIGINAL SOURCE:

(xi) SEQUENCE DESCRIPTION: SEQ ID NO:48:

```
Cys  Arg  Lys  His  Glu  Leu  Tyr  Val  Ser  Phe  Gln  Asp  Leu  Gly  Trp  Gln
 1                   5                        10                          15
```

```
Asp Trp Ile Ile Ala Pro Lys Gly Tyr Ala Ala Asn Tyr Cys Asp Gly
            20                  25                      30

Glu Cys Ser Phe Pro Leu Asn Ala His Met Asn Ala Thr Asn His Ala
        35                  40                  45

Ile Val Gln Thr Leu Val His Leu Met Asn Pro Glu Tyr Val Pro Lys
        50              55                  60

Pro Cys Cys Ala Pro Thr Lys Leu Asn Ala Ile Ser Val Leu Tyr Phe
65                  70                  75                      80

Asp Asp Asn Ser Asn Val Ile Leu Lys Lys Tyr Arg Asn Met Val Val
                85                  90                  95

Arg Ala Cys Gly Cys His Glu
                100
```

( 2 ) INFORMATION FOR SEQ ID NO:49:

( i ) SEQUENCE CHARACTERISTICS:
      ( A ) LENGTH: 103 amino acids
      ( B ) TYPE: amino acids
      ( C ) STRANDEDNESS: single
      ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: C-terminal ( v i ) ORIGINAL SOURCE:

( x i ) SEQUENCE DESCRIPTION: SEQ ID NO:49:

```
Cys Gln Met Gln Thr Leu Tyr Ile Asp Phe Lys Asp Leu Gly Trp His
1               5                   10                  15

Asp Trp Ile Ile Ala Pro Glu Gly Tyr Gly Ala Phe Tyr Cys Ser Gly
            20                  25                      30

Glu Cys Asn Phe Pro Leu Asn Ala His Met Asn Ala Thr Asn His Ala
        35                  40                  45

Ile Val Gln Thr Leu Val His Leu Leu Glu Pro Lys Lys Val Pro Lys
        50              55                  60

Pro Cys Cys Ala Pro Thr Arg Leu Gly Ala Ile Pro Val Leu Tyr His
65                  70                  75                      80

Leu Asn Asp Glu Asn Val Asn Leu Lys Lys Tyr Arg Asn Met Ile Val
                85                  90                  95

Lys Ser Cys Gly Cys His Ala
                100
```

( 2 ) INFORMATION FOR SEQ ID NO:50:

( i ) SEQUENCE CHARACTERISTICS:
      ( A ) LENGTH: 102 amino acids
      ( B ) TYPE: amino acids
      ( C ) STRANDEDNESS: single
      ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: C-terminal ( v i ) ORIGINAL SOURCE:

( x i ) SEQUENCE DESCRIPTION: SEQ ID NO:50:

| Cys | Arg | Arg | His | Ser | Leu | Tyr | Val | Asp | Phe | Ser | Asp | Val | Gly | Trp | Asp |
|---|---|---|---|---|---|---|---|---|---|---|---|---|---|---|---|
| 1 | | | | 5 | | | | | 10 | | | | | 15 | |

| Asp | Trp | Ile | Val | Ala | Pro | Leu | Gly | Tyr | Asp | Ala | Tyr | Tyr | Cys | His | Gly |
|---|---|---|---|---|---|---|---|---|---|---|---|---|---|---|---|
| | | | 20 | | | | | 25 | | | | | 30 | | |

| Lys | Cys | Pro | Phe | Pro | Leu | Ala | Asp | His | Phe | Asn | Ser | Thr | Asn | His | Ala |
|---|---|---|---|---|---|---|---|---|---|---|---|---|---|---|---|
| | | 35 | | | | | 40 | | | | | 45 | | | |

| Val | Val | Gln | Thr | Leu | Val | Asn | Asn | Met | Asn | Pro | Gly | Lys | Val | Pro | Lys |
|---|---|---|---|---|---|---|---|---|---|---|---|---|---|---|---|
| | 50 | | | | | 55 | | | | | 60 | | | | |

| Ala | Cys | Cys | Val | Pro | Thr | Gln | Leu | Asp | Ser | Val | Ala | Met | Leu | Tyr | Leu |
|---|---|---|---|---|---|---|---|---|---|---|---|---|---|---|---|
| 65 | | | | | 70 | | | | | 75 | | | | | 80 |

| Asn | Asp | Gln | Ser | Thr | Val | Val | Leu | Lys | Asn | Tyr | Gln | Glu | Met | Thr | Val |
|---|---|---|---|---|---|---|---|---|---|---|---|---|---|---|---|
| | | | | 85 | | | | | 90 | | | | | 95 | |

| Val | Gly | Cys | Gly | Cys | Arg |
|---|---|---|---|---|---|
| | | | 100 | | |

( 2 ) INFORMATION FOR SEQ ID NO:51:

( i ) SEQUENCE CHARACTERISTICS:
        ( A ) LENGTH: 102 amino acids
        ( B ) TYPE: amino acids
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: C-terminal ( v i ) ORIGINAL SOURCE:

( x i ) SEQUENCE DESCRIPTION: SEQ ID NO:51:

| Cys | Ser | Arg | Lys | Ala | Leu | His | Val | Asn | Phe | Lys | Asp | Met | Gly | Trp | Asp |
|---|---|---|---|---|---|---|---|---|---|---|---|---|---|---|---|
| 1 | | | | 5 | | | | | 10 | | | | | 15 | |

| Asp | Trp | Ile | Ile | Ala | Pro | Leu | Glu | Tyr | Glu | Ala | Phe | His | Cys | Glu | Gly |
|---|---|---|---|---|---|---|---|---|---|---|---|---|---|---|---|
| | | | 20 | | | | | 25 | | | | | 30 | | |

| Leu | Cys | Glu | Phe | Pro | Leu | Arg | Ser | His | Leu | Glu | Pro | Thr | Asn | His | Ala |
|---|---|---|---|---|---|---|---|---|---|---|---|---|---|---|---|
| | | 35 | | | | | 40 | | | | | 45 | | | |

| Val | Ile | Gln | Thr | Leu | Met | Asn | Ser | Met | Asp | Pro | Glu | Ser | Thr | Pro | Pro |
|---|---|---|---|---|---|---|---|---|---|---|---|---|---|---|---|
| | 50 | | | | | 55 | | | | | 60 | | | | |

| Thr | Cys | Cys | Val | Pro | Thr | Arg | Leu | Ser | Pro | Ile | Ser | Ile | Leu | Phe | Ile |
|---|---|---|---|---|---|---|---|---|---|---|---|---|---|---|---|
| 65 | | | | | 70 | | | | | 75 | | | | | 80 |

| Asp | Ser | Ala | Asn | Asn | Val | Val | Tyr | Lys | Gln | Tyr | Glu | Asp | Met | Val | Val |
|---|---|---|---|---|---|---|---|---|---|---|---|---|---|---|---|
| | | | | 85 | | | | | 90 | | | | | 95 | |

| Glu | Ser | Cys | Gly | Cys | Arg |
|---|---|---|---|---|---|
| | | | 100 | | |

( 2 ) INFORMATION FOR SEQ ID NO:52:

( i ) SEQUENCE CHARACTERISTICS:
        ( A ) LENGTH: 104 amino acids
        ( B ) TYPE: amino acids
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO (v) FRAGMENT TYPE: C-terminal (vi) ORIGINAL SOURCE:

(xi) SEQUENCE DESCRIPTION: SEQ ID NO:52:

```
Cys Arg Gln Gln Phe Tyr Ile Asp Phe Arg Leu Ile Gly Trp Asn Asp
 1               5                  10                  15
Trp Ile Ile Ala Pro Ala Gly Tyr Tyr Gly Asn Tyr Cys Glu Gly Ser
            20                  25                  30
Cys Pro Ala Tyr Leu Ala Gly Val Pro Gly Ser Ala Ser Ser Phe His
         35                  40                  45
Thr Ala Val Val Asn Gln Tyr Arg Met Arg Gly Leu Asn Pro Gly Thr
     50                  55                  60
Val Asn Ser Cys Cys Ile Pro Thr Lys Leu Ser Thr Met Ser Met Leu
65                  70                  75                  80
Tyr Phe Asp Asp Glu Tyr Asn Ile Val Lys Arg Asp Val Pro Asn Met
                 85                  90                  95
Ile Val Asp Glu Cys Gly Cys Ala
                100
```

(2) INFORMATION FOR SEQ ID NO:53:

(i) SEQUENCE CHARACTERISTICS:
        (A) LENGTH: 103 amino acids
        (B) TYPE: amino acids
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: C-terminal (vi) ORIGINAL SOURCE:

(xi) SEQUENCE DESCRIPTION: SEQ ID NO:53:

```
Cys Arg Arg Thr Ser Leu His Val Asn Phe Lys Glu Ile Gly Trp Asp
 1               5                  10                  15
Ser Trp Ile Ile Ala Pro Lys Asp Tyr Glu Ala Phe Glu Cys Lys Gly
            20                  25                  30
Gly Cys Phe Phe Pro Leu Thr Asp Asn Val Thr Pro Thr Lys His Ala
         35                  40                  45
Ile Val Gln Thr Leu Val His Leu Gln Asn Pro Lys Lys Ala Ser Lys
     50                  55                  60
Ala Cys Cys Val Pro Thr Lys Leu Asp Ala Ile Ser Ile Leu Tyr Lys
65                  70                  75                  80
Asp Asp Ala Gly Val Pro Thr Leu Ile Tyr Asn Tyr Glu Gly Met Lys
                 85                  90                  95
Val Ala Glu Cys Gly Cys Arg
                100
```

(2) INFORMATION FOR SEQ ID NO:54:

(i) SEQUENCE CHARACTERISTICS:
        (A) LENGTH: 101 amino acids
        (B) TYPE: amino acids
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: C-terminal (vi) ORIGINAL SOURCE:

(xi) SEQUENCE DESCRIPTION: SEQ ID NO:54:

| Cys | Arg | Arg | Val | Lys | Phe | Gln | Val | Asp | Phe | Asn | Leu | Ile | Gly | Trp | Gly |
|---|---|---|---|---|---|---|---|---|---|---|---|---|---|---|---|
| 1 | | | | 5 | | | | | 10 | | | | | 15 | |
| Ser | Trp | Ile | Ile | Tyr | Pro | Lys | Gln | Tyr | Asn | Ala | Tyr | Arg | Cys | Glu | Gly |
| | | | 20 | | | | 25 | | | | | | 30 | | |
| Glu | Cys | Pro | Asn | Pro | Val | Gly | Glu | Glu | Phe | His | Pro | Thr | Asn | His | Ala |
| | | | 35 | | | | 40 | | | | | 45 | | | |
| Tyr | Ile | Gln | Ser | Leu | Leu | Lys | Arg | Tyr | Gln | Pro | His | Arg | Val | Pro | Ser |
| | 50 | | | | | 55 | | | | | 60 | | | | |
| Thr | Cys | Cys | Ala | Pro | Val | Lys | Thr | Lys | Pro | Leu | Ser | Met | Leu | Tyr | Val |
| 65 | | | | | 70 | | | | | 75 | | | | | 80 |
| Asp | Asn | Gly | Arg | Val | Leu | Leu | Glu | His | His | Lys | Asp | Met | Ile | Val | Glu |
| | | | | 85 | | | | | 90 | | | | | 95 | |
| Glu | Cys | Gly | Cys | Leu | | | | | | | | | | | |
| | | | | 100 | | | | | | | | | | | |

(2) INFORMATION FOR SEQ ID NO:55:

(i) SEQUENCE CHARACTERISTICS:
        (A) LENGTH: 109 amino acids
        (B) TYPE: amino acids
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: C-terminal (vi) ORIGINAL SOURCE:

(ix) FEATURE:
        (A) NAME/KEY: Other
        (B) LOCATION: 2...2
        (D) OTHER INFORMATION: any given amino acid residue
        (A) NAME/KEY: Other
        (B) LOCATION: 4...5
        (D) OTHER INFORMATION: any given two amino acid residues
        (A) NAME/KEY: Other
        (B) LOCATION: 11...11
        (D) OTHER INFORMATION: any given amino acid residue
        (A) NAME/KEY: Other
        (B) LOCATION: 13...13
        (D) OTHER INFORMATION: any given amino acid residue
        (A) NAME/KEY: Other
        (B) LOCATION: 16...16
        (D) OTHER INFORMATION: any given amino acid residue
        (A) NAME/KEY: Other
        (B) LOCATION: 23...23
        (D) OTHER INFORMATION: any given amino acid residue
        (A) NAME/KEY: Other
        (B) LOCATION: 26...26
        (D) OTHER INFORMATION: any given amino acid residue
        (A) NAME/KEY: Other
        (B) LOCATION: 28...28
        (D) OTHER INFORMATION: any given amino acid residue
        (A) NAME/KEY: Other
        (B) LOCATION: 31...31
        (D) OTHER INFORMATION: any given amino acid residue
        (A) NAME/KEY: Other
        (B) LOCATION: 33...33

( D ) OTHER INFORMATION: any given amino acid residue
( A ) NAME/KEY: Other
( B ) LOCATION: 35...35
( D ) OTHER INFORMATION: any given amino acid residue
( A ) NAME/KEY: Other
( B ) LOCATION: 39...40
( D ) OTHER INFORMATION: any given two amino acid residues
( A ) NAME/KEY: Other
( B ) LOCATION: 41...42
( D ) OTHER INFORMATION: any given two amino acid residues
( A ) NAME/KEY: Other
( B ) LOCATION: 44...44
( D ) OTHER INFORMATION: any given amino acid residue
( A ) NAME/KEY: Other
( B ) LOCATION: 46...49
( D ) OTHER INFORMATION: absent or any given 1 to 4 amino acid
residues
( A ) NAME/KEY: Other
( B ) LOCATION: 59...62
( D ) OTHER INFORMATION: any given four amino acid residues
( A ) NAME/KEY: Other
( B ) LOCATION: 63...63
( D ) OTHER INFORMATION: absent or any given amino acid residue
( A ) NAME/KEY: Other
( B ) LOCATION: 64...65
( D ) OTHER INFORMATION: any given two amino acid residues
( A ) NAME/KEY: Other
( B ) LOCATION: 78...79
( D ) OTHER INFORMATION: any given two amino acid residues
( A ) NAME/KEY: Other
( B ) LOCATION: 82...82
( D ) OTHER INFORMATION: any given amino acid residue
( A ) NAME/KEY: Other
( B ) LOCATION: 85...85
( D ) OTHER INFORMATION: any given amino acid residue
( A ) NAME/KEY: Other
( B ) LOCATION: 87...89
( D ) OTHER INFORMATION: any given three amino acid residues
( A ) NAME/KEY: Other
( B ) LOCATION: 91...91
( D ) OTHER INFORMATION: absent or any given amino acid residue
( A ) NAME/KEY: Other
( B ) LOCATION: 96...96
( D ) OTHER INFORMATION: any given amino acid residue
( A ) NAME/KEY: Other
( B ) LOCATION: 98...99
( D ) OTHER INFORMATION: any given two amino acid residues
( A ) NAME/KEY: Other
( B ) LOCATION: 103...104
( D ) OTHER INFORMATION: any given two amino acid residues
( A ) NAME/KEY: Other
( B ) LOCATION: 109...109
( D ) OTHER INFORMATION: absent or any given amino acid residue ( x i ) SEQUENCE DESCRIPTION: SEQ ID NO:55:

```
Cys Xaa Arg Xaa Xaa Leu Tyr Val Asp Phe Xaa Asp Xaa Gly Trp Xaa
 1               5                  10                  15

Asp Trp Ile Ile Ala Pro Xaa Gly Tyr Xaa Ala Xaa Tyr Cys Xaa Gly
             20                  25                  30

Xaa Cys Xaa Phe Pro Leu Xaa Xaa Xaa Xaa Asn Xaa Thr Xaa Xaa Xaa
         35                  40                      45

Xaa Asn His Ala Ile Val Gln Thr Leu Val Xaa Xaa Xaa Xaa Xaa Pro
     50                  55                  60

Xaa Xaa Val Pro Lys Pro Cys Cys Val Pro Thr Lys Leu Xaa Xaa Ile
 65              70                  75                      80

Ser Xaa Leu Tyr Xaa Asp Xaa Xaa Xaa Asn Xaa Val Val Leu Lys Xaa
                 85                  90                  95

Tyr Xaa Xaa Met Val Val Xaa Xaa Cys Gly Cys Arg Xaa
             100             105
```

( 2 ) INFORMATION FOR SEQ ID NO:56:

( i ) SEQUENCE CHARACTERISTICS:
   ( A ) LENGTH: 4 amino acids
   ( B ) TYPE: amino acids
   ( C ) STRANDEDNESS: single
   ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:56:

Arg Xaa Xaa Arg
1

PRODUCTION AND USE OF ANTI-DORSALIZING MORPHOGENETIC PROTEIN

FIELD OF THE INVENTION

The present invention relates to the production and use of a member of the TGF-β superfamily, termed anti-dorsalizing morphogenetic protein. More specifically, the invention relates to an isolated polynucleotide coding for vertebrate anti-dorsalizing morphogenetic protein, a recombinant vertebrate anti-dorsalizing morphogenetic protein, and to a method of treatment for a medical condition involving inappropriate proliferation of tissues.

BACKGROUND ART

Initial interest in the Bone Morphogenetic Proteins (BMPs), a group within the TGF-β superfamily (Kingsley (1994) *Genes Dev.* 8:133–146) resulted from their ability to initiate endochondral bone formation in adult animals (Urist (1965) *Science* 150:893–899). Purification and sequencing of protein with bone inductive activity led to the discovery of a family of growth factors (Wozney, et al. (1988) *Science* 242:1528–1534; Wang, et al. (1988) *Proc. Natl. Acad. Sci. USA* 85:9484–9488; Hammonds, et al. (1991) *Mol. Endocrinol.* 5:149–155; Sampath, et al. (1992) *J. Biol. Chem.* 267:20352–20362) resembling the Drosophila dpp gene (Padgett, et al. (1987) *J. Biol. Chem.* 265:17281–17284) and Vg1 (Weeks and Melton (1987) *Cell* 51:861–867). These genes encoded TGF-β homologs that had been implicated in embryonic body axis determination. Experiments with recombinant proteins indicated that single BMPs were sufficient to induce this complex cascade of events in adult vertebrates (Wozney, et al. (1988) *Science* 242:1528–1534). Subsequently, many related proteins were identified and found to participate in a wide variety of developmental processes (for review, see Kingsley (1994) *Genes Dev.* 8:133–146). These findings complemented the discovery of additional dorsalizing (Smith and Harland (1992) *Cell* 70:829–840; Niehrs, et al. (1993) *Cell* 72:491–503) and mesoderm-inducing (Smith and Harland (1991) *Cell* 67:753–765) peptide growth factors.

BRIEF DESCRIPTION OF THE FIGURES

FIG. 1 shows nucleotide (SEQ ID NO:1) and deduced amino acid sequences of ADMP-1. The entire nucleotide sequence is SEQ ID NO:7. The nucleotide coding sequence and deduced amino acid sequence are SEQ ID NOS: 1 and 2, respectively.

FIG. 3 shows amino acid alignment of ADMP-1 SEQ ID NO:40 with other TGF-β proteins. BMP-3 (SEQ ID NO: 41); BMP-2 (SEQ ID NO: 42); BMP-4 (SEQ ID NO: 43); Veg (SEQ ID NO: 44); GDF-1 (SEQ ID NO: 45); BMP-5 (SEQ ID NO: 46); BMP-7 (SEQ ID NO: 47); BMP-6 (SEQ ID NO: 48); 60A (SEQ ID NO: 49); dpp (SEQ ID NO: 50); GDF-5 (SEQ ID NO: 51); activin B (SEQ ID NO: 52); dorsalin (SEQ ID NO: 53); nodal (SEQ ID NO: 54) and the consensus sequence (SEQ ID NO: 55).

SUMMARY OF THE INVENTION

Figure 2:
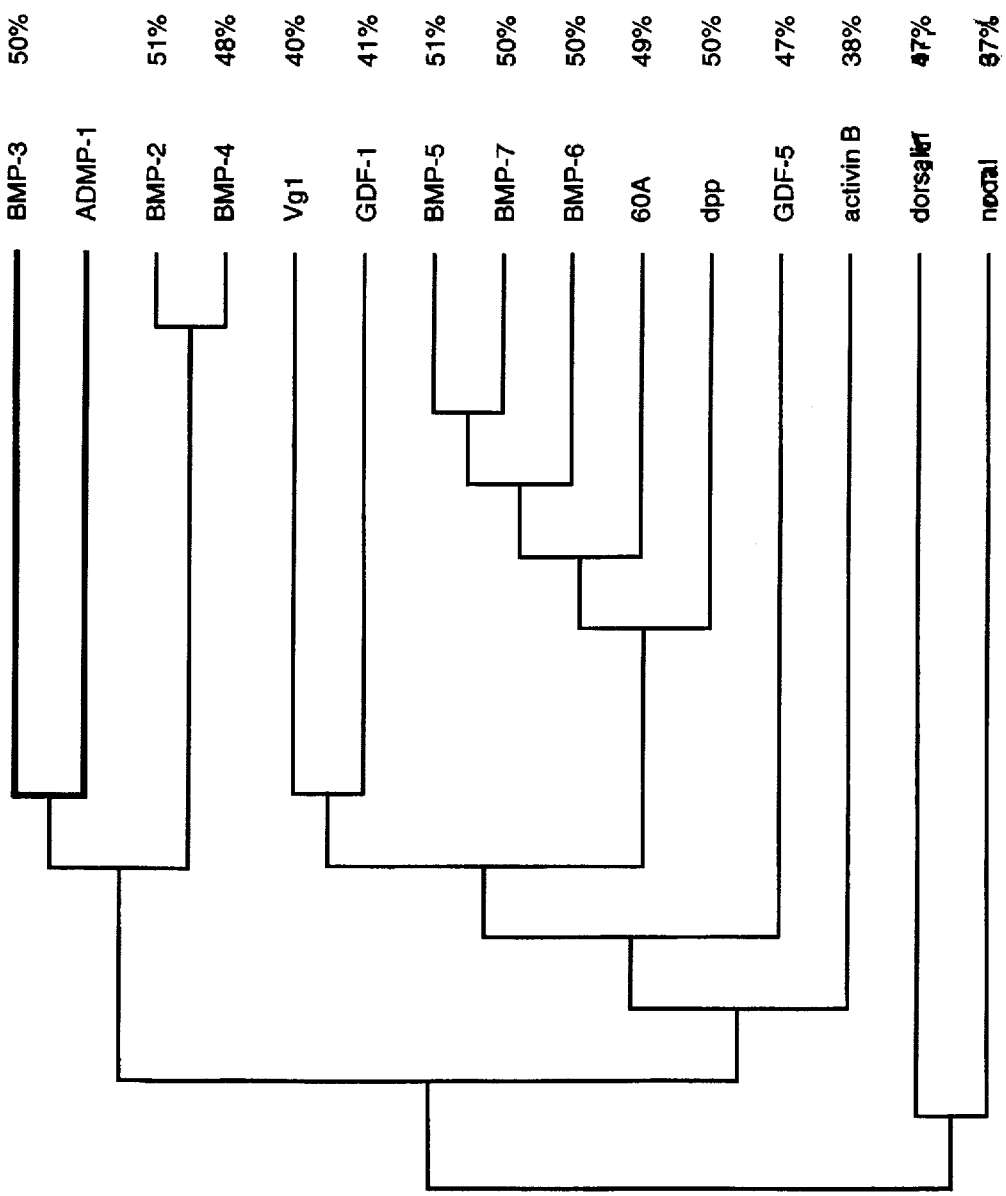
FIG. 2 shows schematic representation of the relationship between ADMP-1 and other members of the TGF-β superfamily.

The present inventors have identified a novel growth factor that is designated Anti-Dorsalizing Morphogenetic Protein-1 (ADMP-1) which is most closely related to human BMP-3. ADMP-1 has a unique function serving to counterbalance dorsalizing influences homeostatically in Xenopus, and homologous counterparts thereof are present universally in vertebrates. ADMP-1 can be effectively used for treatment of syndromes involving inappropriate proliferation of tissues, such as neuroblastomas, neuromas, neurofibromatoses, and so forth. Like other master gene regulatory proteins, the unique effects of ADMP-1 are concentration-dependent.

One aspect of the present invention is an isolated polynucleotide having the sequence indicated as SEQ ID NO:1 coding for an anti-dorsalizing morphogenetic protein.

Another aspect of the present invention is an isolated recombinant anti-dorsalizing morphogenetic protein obtained by expression of a polynucleotide having the sequence indicated as SEQ ID NO:1.

Still another aspect of the present invention is an isolated recombinant anti-dorsalizing morphogenetic protein having the amino acid sequence indicated as SEQ ID NO:2. The growth factor having the above amino acid sequence and the nucleotide sequence coding therefor are novel, which are similar to those of BMP-3, but have unique functions such as suppression of neural crest derivatives.

Yet another aspect of the present invention is an isolated polynucleotide from mammalian genomic DNA or cDNA libraries, having a sequence homologous to the sequence indicated as SEQ ID NO:1 coding for a anti-dorsalizing morphogenetic protein. There is the overwhelming likelihood of occurrence of a member of the BMP family throughout the vertebrates, and the presence of ADMP-1 in humans has been confirmed.

A still further aspect of the present invention is a pharmaceutical preparation for treatment of a medical condition involving inappropriate proliferation of tissues, comprising an isolated recombinant anti-dorsalizing morphogenetic protein having the amino acid sequence indicated as SEQ ID NO:2 or a homolog thereto, and a pharmaceutically acceptable carrier.

Yet one more aspect of the present invention is a method of treatment for a medical condition involving inappropriate proliferation of tissues, comprising administering to the tissues an amount of an isolated recombinant anti-dorsalizing morphogenetic protein having the amino acid sequence indicated as SEQ ID NO:2 or a homolog thereto sufficient to prevent appearance of inappropriate proliferation of the tissues. Medical conditions, i.e., syndromes associated with neural crest derivatives such as neuroblastomas, neuromas and neurofibromatoses can be exemplified.

An additional aspect of the present invention is a method for isolating a vertebrate anti-dorsalizing morphogenetic protein from a vertebrate genomic DNA or cDNA library by PCR using primers to SEQ ID NOs:3 and 4, and screening the vertebrate library using the cloned PCR products as a probe to obtain a polynucleotide of the vertebrate anti-dorsalizing morphogenetic protein. Since the amino acid sequence of the protein is well conserved throughout vertebrates including humans, it is possible to probe various mammalian genomic DNA or cDNA libraries using the conserved region of the gene of other vertebrates such as Xenopus. That is, the above primers can be used as universal primers to obtain a probe for the cloning of various vertebrate ADMP-1.

DETAILED DESCRIPTION OF THE PREFERRED EMBODIMENTS

As discussed above, many related proteins have been identified and found to participate in a wide variety of developmental processes. Since noggin (Lamb, et al. (1993) *Science* 262:713–718), GDNF (Lin, et al. (1993) *Science* 260:1130–1132), and dorsalin (Basler, et al. (1993) *Cell* 73:687–702) appear to support differentiation of nervous system components in vitro, the possibility that diffusible factors might act to instruct nearby cells to adopt a neural form suggested a molecular link to classic observations concerning neural development. (See, e.g., Spemann and Mangold (1924) *Roux's Arch. Entwench* 100:599–638).

Notwithstanding the foregoing, the concept that neural induction requires instructive interactions has recently been challenged. As pointed out by Hemmati-Brivanlou and Melton (Hemmati-Brivanlou and Melton (1994) *Nature* 359:609–614), dissociated and reaggregated animal cap cells adopt a neural fate (Sato and Sargent (1989) *Dev. Biol.* 134:263–266). One interpretation of this result is that disaggregation dilutes a signal that suppresses neural differentiation. Direct evidence that such signaling molecules exist and may resemble activin, another member of the TGF-β superfamily, has been presented recently. If a truncated activin receptor (ΔXAR1) message is injected into Xenopus embryos, their anterior and neural structures are augmented, and injected ventral blastomeres adopt a dorsal fate (Hemmati-Brivanlou and Melton (1994) *Nature* 359:609–614). Furthermore, when mRNA encoding follistatin, an antagonist of activin and perhaps related proteins, is overexpressed, embryos are neuralized directly (Hemmati-Brivanlou, et al. (1994) *Nature* 359:609–614). Taken together, these observations suggest that one or more activin-like molecules normally present in the animal region of the embryo may act to divert dorsal cells from a default neural fate. The physiological role of such a signal may be to moderate, or resist (Dawid (1994) *J. Biol. Chem.* 269:6259–6262) other dorsalizing signals that form parts of a complex homeostatic mechanism.

Considering homeostatic mechanisms, various growth factors may be present in tissues in which differentiation or proliferation takes place. A growth factor which produces effects opposite to those of follistatin and the truncated activin receptor, which produces profound suppression of neural structures, downregulates known dorsalizing signals, and is induced by dorsalizing perturbations, has heretofore not been described.

ADMP-1: A Novel Member Of the TGF-β Superfamily

Many members of the TGF-β superfamily are currently being evaluated as human therapeutic agents in various mammalian models. Since these experimental systems have limited ability to discriminate between various members of the BMP family and do not allow access to events in early vertebrate development, the present inventors explored the ability of paradigms developed in Xenopus to complement ongoing work in other systems. In the course of these investigations, the present inventors identified a novel growth factor expressed in dorsal and neural structures of Xenopus embryos that has structural characteristics of the Bone Morphogenetic Proteins. It is the first member of the TGF-β family of peptide growth factors to be identified in the Spemann organizer. Because overexpression of the gene results in down regulation of known dorsalizing factors and results in ventralization of affected embryos, we term the factor Anti-Dorsalizing Morphogenetic Protein-1 (ADMP-1). Its properties are consistent with those expected for the endogenous neurostatic activity suggested by experiments with a truncated activin receptor and follistatin.

Figure 1:
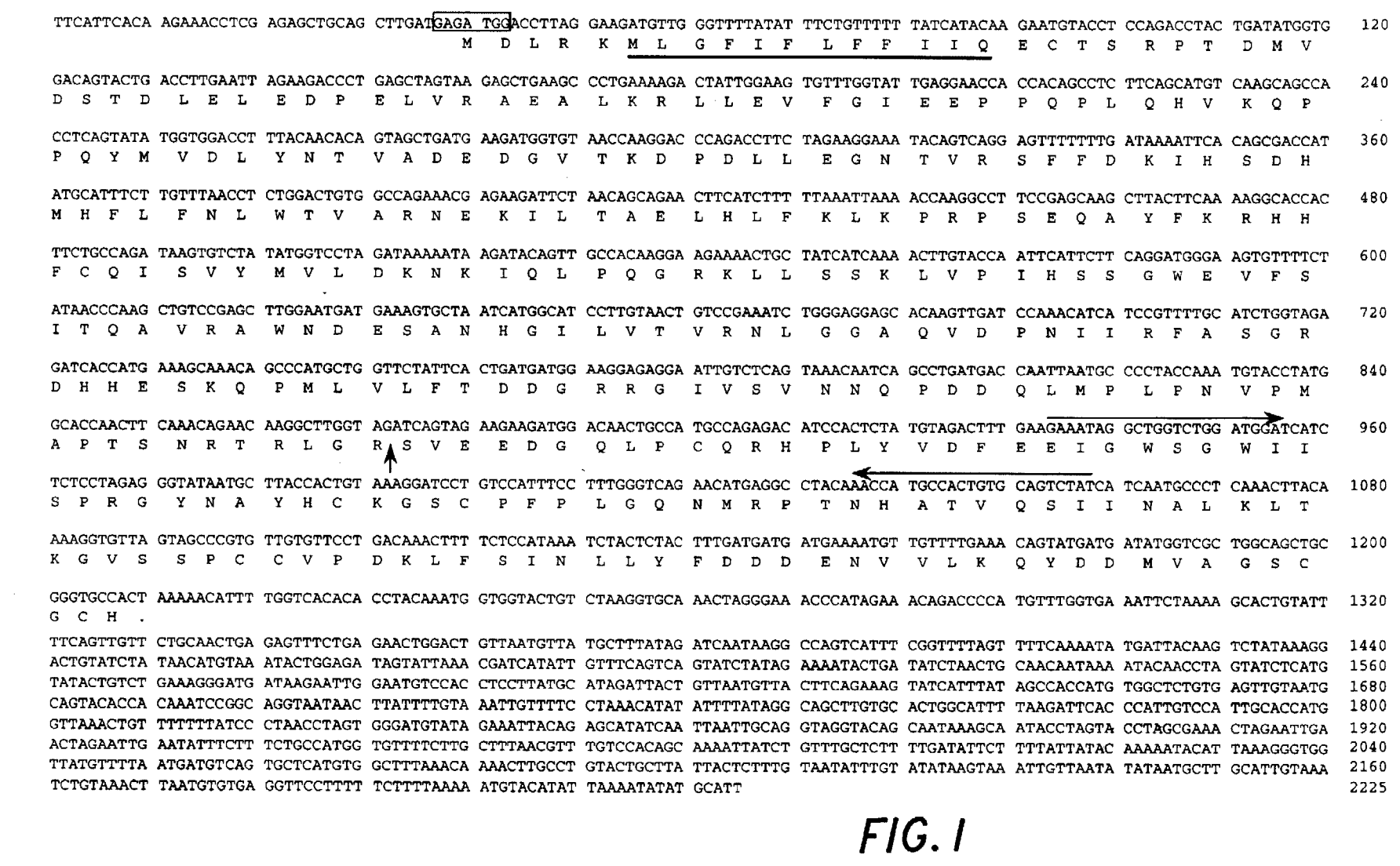

The complete 2225 bp sequence (SEQ ID NO:7, FIG. 1) including a 1700 bp polynucleotide coding for ADMP-1 (SEQ ID NO:1) has a consensus translation initiation site (Kozak (1991) *J Biol Chem* 266, 12867–19870) and putative signal sequence (von Heijne (1986) *Nucl. Acids Res.* 14:4683–4690). The deduced amino acid sequence (SEQ ID NO:2) contains all features characteristic of the BMP family, including a consensus RXXR SEQ ID NO:56 proteolytic processing site (Özkaynak et al. (1992) *J. Biol. Chem.* 267:25220–25227) followed by a carboxy-terminal domain with seven highly conserved cysteine residues at the positions observed in the majority of these proteins (Kingsley (1994) *Genes Dev.* 8:133–146, and Reddi (1992) *Curr. Opin. Cell Biol.* 4:850–855). The carboxy terminal region following the first of the seven conserved cysteines demonstrates 50% identity with BMP-3 and several other members of this gene family (FIGS. 2 and 3, SEQ ID NOs:40–55). Most of the BMPs so far identified demonstrate at least 90% amino acid identity between mammalian and lower vertebrate homologs.

Isolation of ADMP-1 cDNA

Based on highly conserved regions of the amino acid sequence of ADMP-1 throughout vertebrates, degenerate primers biased to detect homologs of the mammalian BMP-3 gene can be used to amplify sequences from a vertebrate (such as Xenopus) genomic DNA library, using conditions described previously (Wharton, et al. (1991) *Proc. Natl. Acad. Sci. USA* 88:9214–9218). For example, the 5' oligonucleotide may have the sequence SEQ ID NO:3, and the 3' oligonucleotide may have the sequence SEQ ID NO:4. The amplified products are then cloned into an appropriate vector such as PCR II vector (Invitrogen, San Diego, Calif.), and hybridization probes are prepared. The vertebrate cDNA library is screened by plaque hybridization using the probes. The clones thus obtained are ligated to an anchor oligonucleotide as necessary, and amplified using primers such as SEQ ID NOs:5 and 6 complementary to the anchor oligonucleotide and to sequences from the clone to yield a complete open reading frame and translation initiation site.

Isolation of Mammalian ADMP-1 cDNA

Existing evidence indicates overwhelming likelihood of occurrence of any given member of the BMP family throughout vertebrates. For example, the present inventors have obtained a muscle-specific hybridization signal using the Xenopus gene to probe human multiple tissue RNA blots. ADMP-1 proves no exception. To isolate a mammalian clone such as the human clone, a PCR fragment prepared from the conserved (carboxyl-terminal) region of the gene can be used to probe a mammalian genomic library. For example, the same probe as that used in Xenopus (SEQ ID NOs:3 and 4) can be used to screen a P1 plasmid library.

Functions of ADMP-1 as Member of TGF-β Superfamily

The identified novel gene, ADMP-1, has characteristics of the Bone Morphogenetic Protein group of peptide growth factors. Its peak of expression is earlier than that of any other member of the TGB-β superfamily for which comparable data are available, and it is the first of these proteins to show such predominant localization at the Spemann organizer. Unlike other factors normally expressed in this location during gastrulation (e.g., noggin (Smith and Harland (1992) *Cell* 67:753–765, goosecold (Cho, et al. (1991) *Cell* 67:1111–1120, follistatin (Hemmati-Brivanlou, et al. (1994) *Cell* 77:283–295.), ADMP-1 demonstrates potent ventralizing activity. Injection of ADMP-1 message into dorsal blastomeres does not produce obvious abnormalities during gastrulation, but does suppress development of dorsoanterior structures, including those of neural crest origin. Hybridization in situ and lineage labeling experiments together indicate that development of an abnormal phenotype requires overexpression of the gene in the regions where it is normally localized.

Figure 7A:
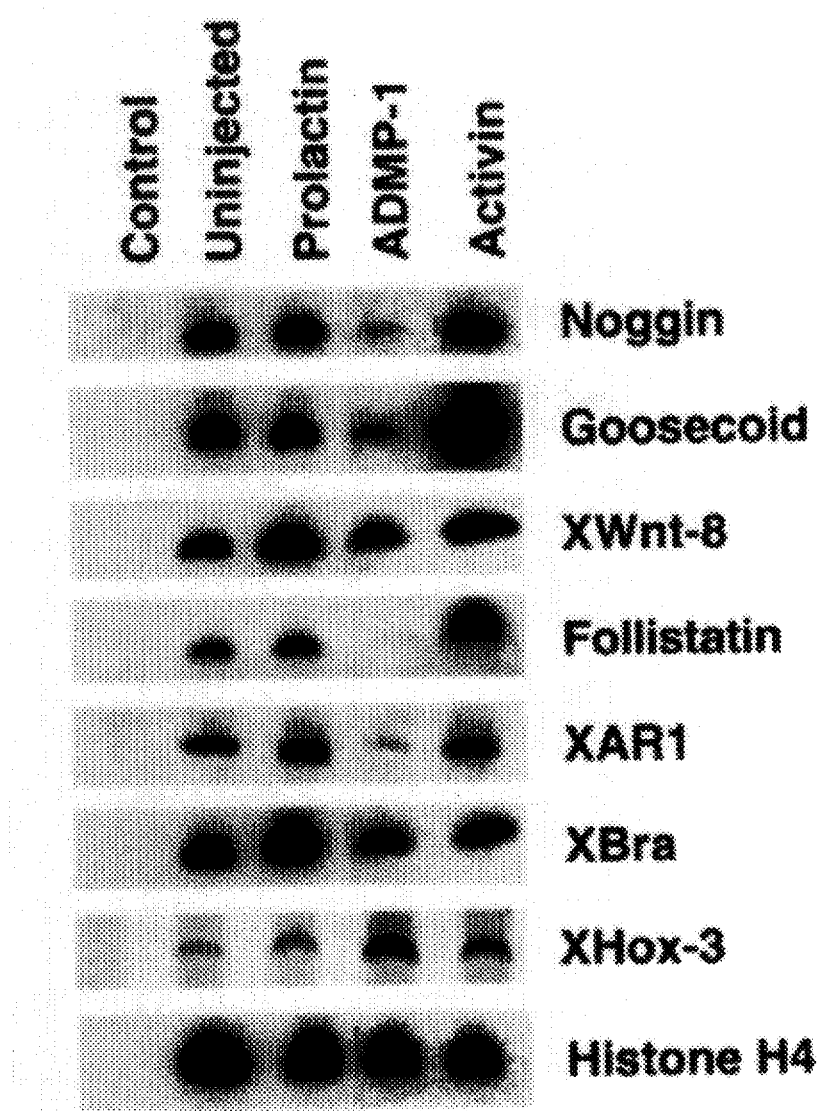
FIG. 7 shows downregulation of Dorsalizing Signals and Dorsal Makers by ADMP-1. Stage 10 (A) or stage 17 (B) embryos were assayed for expression in the indicated genes by RT-PCR following injection of ADMP-1 message. In (C), total ADMP-1 in animal cap was assayed.

RT-PCR assays of ADMP-1 injected embryos clearly indicate inhibition of noggin, goosecold, and follistatin expression; effects on the ventral marker XWnt-8 and the general mesodermal marker XBra are less pronounced (FIG. 7(A)). These effects are consistent with a ventralized phenotype and suppression of dorsal markers MyoD a, MyoD b, Twist, NCAM, cardiac actin, and muscle actin (FIG. 7(B)) observed in response to ADMP-1 overexpression. Moreover, injection of ADMP-1 message blocks the dorsalizing effect of lithium chloride.

Lithium chloride and activin have both been shown to induce dorsal structures (Kao and Elinson (1988) *Dev. Biol.* 127:64–77; Sokol, et al. (1990) *Science* 249:561–564; Thomsen, et al. (1990) *Cell* 63:485–493) and dorsalizing signals (FIG. 7A, (Steinbeisser, et al. (1993) *Development* 118:499–507; Hemmati-Brivanlou, et al. (1994) *Cell* 77:273–281). Nevertheless, LiCl treatment causes a 4–8 fold increase in ADMP-1 expression, and injected activin mRNA produces an even greater effect. Since direct over-expression of ADMP-1 leads to decreased expression of dorsalizing signals and a ventralized phenotype, induction of this gene is likely to be a secondary effect, perhaps to provide a negative regulatory response to the dorsalizing perturbations. The fact that UV irradiation, which ventralizes embryos, leads to decreased expression of ADMP-1 is consistent with this concept.

Comparison of the effects of injected ADMP-1 message to those observed when follistatin or truncated activin receptor are overexpressed supports the above descriptions. Injection of ventral blastomeres with ΔXAR1 (Hemmati-Brivanlou and Melton (1994) *Cell* 77:273–281 ) converts progeny cells to a dorsal fate, injection of ventral cells with ADMP-1 is without effect, and injection of dorsal cells ventralizes their progeny. Furthermore, overexpression of ΔXAR1 produces embryos with exaggerated neuralization, which is opposite the ADMP-1 phenotype. The effects of ADMP-1 and ΔXAR1 message on expression of the neural marker NCAM are also opposite.

Unlike activin, ADMP-1 is expressed during gastrulation in amounts readily detectable on RNA blots. Its spatial domain of expression parallels that of the most potent dorsalizing signals identified to date. It is therefore present at the correct time and place to influence dorsoanterior patterning and neural induction. Since the phenotypic and molecular consequences of ADMP-1 overexpression are opposite to those produced by these molecules, ADMP-1 is considered to function to provide negative feedback to regulate their effects, and ADMP-1 is considered to represent one candidate for the proposed negative regulatory signal.

Expression of Recombinant Protein

In conducting expression of a recombinant ADMP-1, it should be considered that the gene coding for ADMP-1 tends to form a dimer, and that a secreted protein is susceptible to proteolysis. Indeed, it may require proteolysis at an appropriate site to be biologically active.

Expression of biologically active members of the TGF-β superfamily in bacteria has been reported in two cases: TGF-β2 (Schlunegger, et al. (1992) FEBS Lett 303, 91–93) and GDNF (Lin, et al. (1993) *Science* 260, 1130–1132). In each case, the DNA sequence encoding the mature region of the protein only (i.e., bounded by the RXXR SEQ ID NO: 56 consensus proteolysis site and the stop codon) was subcloned into a bacterial expression vector and the polynucleotide was expressed in bacteria by standard methods. It was then solubilized under denaturing and reducing conditions and gradually allowed to renature and oxidize. A significant proportion of the material folds correctly into native protein. For TGF-β2, this was proven definitively by X-ray crystallography. In this paper, the method cited was a reference to European patent application 0 433 225 A1, by Cerletti, et al. (1991). Since ADMP-1 of the present invention is a member of this homologous gene family, a similar method or modification thereof can be employed to yield an active protein. Other non-mammalian expression systems such as a baculovirous expression system and yeast expression system can also be employed. For example, cDNA coding for ADMP-1 is ligated into a baculovirous expression plasmid such as that taught by Lin, et al. (*Science* 260:1130–1132 (1993)), the disclosure of which is hereby incorporated by reference. Following ligation by standard methods known to those of skill in the art, the plasmid is transfected into an insect strain. Following incubation, the expressed protein is then isolated by standard methods from the cells. An example of recombinantly producing ADMP-1 using a mammalian expression system includes the steps of subcloning the open reading frame into the mammalian expression vector pcDNA III, transfecting cell lines with the clone, and either culturing them by conventional procedures or implanting them in nude mice (*J. Cell Biol.* 126:1595–1609).

Assay Systems for Evaluating ADMP-1

For initial screening, the activity of ADMP-1 can be evaluated in the subcutaneous implantation assay to induce bone, cartilage, fibrous tissue, and/or hematopoietic tissue. This can be done both with material isolated from cell lines and with transfected cells injected into nude mice. It is also possible to assess the ability of the protein to induce mesoderm and molecular markers specific for various types of tissue in the Xenopus animal cap assay (Dawid (1991) *Methods Cell Biol.* 36:311–328), which allows rapid assessment of the ability of various peptide growth factors to influence tissue differentiation. The disclosure of this Dawid reference is incorporated herein by this reference thereto.

Application for Medical Conditions

Overexpression of the gene for ADMP-1 prevents appearance of neural crest derivatives such as in the brain, eyes, ears, and pigment containing cells. Thus, administration of ADMP-1 is believed appropriate for treatment of syndromes involving inappropriate proliferation of tissues, such as neuroblastmas, neuromas, neurofibromatoses, melanomas, psoriasis, and other epithelial hyperplasias. In this connection, the single strong hybridization signal observed when multiple human tissues are probed is to skeletal muscle. At intermediate levels of overexpression, the musculature of the embryos is grossly exaggerated, and the expression levels of molecular markers specific for muscle appear to be elevated. This is reversed at high levels of overexpression. A biphasic pattern of response to activin, another member of this family, has been demonstrated convincingly by several investigators, and it is believed that ADMP-1 has a similar characteristic. In addition, ADMP-1 is muscle inductive at an intermediate dose. Gross exaggerations of muscular structures, modest increases in muscle-specific genes, and specific localization to muscle in human multiple tissue RNA blots all confirm the presence of such activity.

To introduce ADMP-1 into a target site, for example, a recombinant protein with a pharmaceutically acceptable carrier can be applied, in the form of a cream or mist, directly to an epithelium in an amount sufficient to prevent appearance of inappropriate proliferation of the tissues. For injectable preparations for humans, ADMP-1 derived from humans is preferred due to low antigenicity. Alternatively, gene therapy can be used to administer the protein. For example, cDNA coding for ADMP-1 can be inserted into a non-replicative vector which is transfected into cells, whereby the vector is propagated, and the propagated vectors are purified and injected into a target site to be treated. The cells at the target site are infected with the vector and express the gene to produce ADMP-1 at the site. Creation of appropriate vectors, etc. which is well known to those of ordinary skill in the art can be employed.

Diagnostic Use

By using an oligonucleotide having a sequence included in the cDNA coding for ADMP-1 (SEQ ID NO:1) as a PCR primer or hybridization probe, it is possible to diagnose a syndrome associated with inappropriate proliferation of tissues such as those described above in which genetic lesions are involved. As used herein a "lesion" can mean a point mutation, deletion or addition of nucleotides. Deformation or mutation including differentiated cancer tissues can also be diagnosed using the oligonucleotide. The inventors now know that ADMP-1 is necessary for proper development. Accordingly, lesions in the gene encoding this protein are expected to be associated with any of a variety of developmental defects. Thus, the cDNA sequence themselves, either full length or partial length, can be used to diagnose affected or carrier individuals, in utero or postpartum, by standard molecular diagnostic techniques based on analysis of restriction fragment length polymorphisms present in three generations of an affected kindred.

A method of diagnosis of the above syndromes can be conducted based on standard techniques known to those of ordinary skill in the art. For instance, a method of diagnosis of a syndrome associated with inappropriate proliferation of tissues can comprise the steps of collecting a sample containing the tissues from a vertebrate to be tested, isolating polynucleotides from the sample, subjecting the polynucleotides to PCR with Taq DNA polymerase or DNA ligase with the use of an oligonucleotide having a sequence included in the polynucleotide coding for ADMP-1 (SEQ ID NO:1) as a PCR primer, and detecting the presence of a polynucleotide related to inappropriate proliferation of the tissues in the PCR products. Alternatively, the oligonucleotide can be used as a hybridization probe in Southern blotting to detect the presence of a polynucleotide related to inappropriate proliferation of the tissues in the polynucleotides transferred to a membrane. Based on the above method, a bioassay kit for detecting the above syndromes can also be constituted using standard techniques known to those of ordinary skill in the art.

EXPERIMENT 1

Isolation of ADMP-1 cDNA

Degenerate primers biased to detect homologs of the mammalian BMP-3 gene were used to amplify sequences from Xenopus genomic DNA using conditions described previously (Wharton, et al. (1991) Proc. Natl. Acad. Sci. U.S.A. 88:9214–9218). The 5' oligonucleotide was 5'-ATHGGITGGWSNGARTGGATHAT-3'(SEQ ID NO:3); the 3' oligonucleotide was 5'-ATISWYTGRATNGTR GCRTGRTT-3'(SEQ ID NO:4). Amplified fragments were purified by agarose gel electrophoresis, cloned in the PCR II vector (Invitrogen, San Diego, Calif.), and sequenced using standard procedures (Sanger, et al. (1977) Proc. Natl. Acad. Sci. USA 74:5463–5467). Hybridization probes were generated by labeling inserts of interest with dogoxigenin by substituting Dig DNA labeling mix (Boehringer Mannheim) for unmodified dNTPs in PCR reactions as described above. $10^6$ plaques from a stage 13 λgt11 cDNA library (Richter, et al. (1988) Proc. Natl. Acad. Sci. USA 85:8086–8090) were screened using Magnagraph nylon membranes (MSI, Westborough, Mass.) and the Genius™ chemiluminescent detection system (Boehringer Mannheim). The manufacturer's protocol was modified by the addition of a 3 hour wash in 3×SSC/0.1% SDS at 65° C. before the prehybridization step and increasing the concentration of blocking reagent to 5%; the final stringency wash was for 15 minutes at 68° C. in 0.3×SSC/0.1% SDS. Over 30 purified clones were analyzed by restriction digestion, PCR and sequencing from phage plaques. None of the clones contained a translation initiation site or putative transmembrane signal sequence. cDNA from stage 12 embryos was therefore prepared using Superscript II reverse transcriptase (Life Technologies, Gaithersberg, Md.) and ligated to an anchor oligonucleotide (Clontech, Palo Alto, Calif.) with T4 RNA ligase (New England Biolabs, Beverly, Mass.) (Edwards, et al. (1991) Nucl. Acids Res. 19:5227–5232). Primers complementary to the anchor oligonucleotide and to sequences from the clone were used in successive rounds of DNA amplification; the product was sequenced with a solid phase capture technique to complete characterization of the cDNA. One clone contained all but the first 12 nucleotides of the open reading frame. DNA from this clone was amplified with the primers 5'-ATGAGATGGACCTTAGGAAGATGTTGGGTTTTAT ATTTCT-3'(SEQ ID NO:5) and 5'-GGAATTCTTA GTGGCACCCGCAGCTGCC-3'(SEQ ID NO:6) to yield a complete open reading frame and translation initiation site, cloned into pCR Script (Strategene, La Jolla, Calif.) for preparation of in situ hybridization probes, and sequenced. The insert was subcloned into pSP64R1 (available from Sergei Sokol, Harvard University) to provide a template for preparation of capped mRNA for injection experiments. Other similar vectors are available and could be used if necessary, though these are all specifically tailored to Xenopus.

The complete 2225 bp sequence (SEQ ID NO:7, FIG. 1) including a 1700 bp polynucleotide coding for ADMP-1 (SEQ ID NO:1) has a consensus translation initiation site (Kozak (1991) J. Biol. Chem. 266:12867–19870) and putative signal sequence (von Heijne (1986) *Nucl. Acids Res.* 14:4683–4690). The deduced amino acid sequence contains all features characteristic of the BMP family, including a consensus RXXR SEQ ID NO: 56 proteolytic processing site (Özkaynak et al. (1992) *J. Biol. Chem.* 267:25220–25227) followed by a carboxy-terminal domain with seven highly conserved cysteine residues at the positions observed in the majority of these proteins (Kingsley (1994) *Genes Dev.* 8:133–146, and Reddi (1992) *Curr. Opin. Cell Biol.* 4:850–855).

EXPERIMENT 2

Sequence Similarity

Sequence similarity was assessed with the BLAST network service of the National Center for Biotechnology Information (Bethesda, Md.). Alignments were done with Geneworks (Intelligenetics, Mountain View, Calif.). The carboxy terminal region following the first of the seven conserved cysteines (FIG. 3) demonstrates 50% identity with BMP-3 and several other members of this gene family (FIG. 2). Most of the BMPs so far identified demonstrate at least 90% amino acid identity between mammalian and lower vertebrate homologs.

EXPERIMENT 3

Localization of Gene Expression

Preparation of Embryos

South African clawed frogs were maintained and manipulated with methods adapted from those described by Gurdon (Methods in Developmental Biology (1967), Crowell, pp.75–84; Gurdon (1977) *Method Cell Biol.* 16:125–139). Female frogs were primed by injection of 750 units of human chorionic gonadotropin into the dorsal lymph sac and eggs were expressed 8–14 hours later into 0.3×Marc's Modified Ringer's solution (MMR; (Peng (1991) *Method Cell Biol.* 36:657–662)). They were fertilized with testes macerated in 1×MMR, dejellied in 2% L-cysteine brought to pH 7.8 with NaOH (Peng (1991) *Method Cell Biol.* 36:657–662), and cultured in 0.1×MMR supplemented with 50 µg/mL gentamycin. All embryos were staged according to Nieuwkoop and Faber (Nieuwkoop and Faber (1967) Normal table of *Xenopus laevis*, North Holland).

Northern Blots

Total RNA was isolated from staged embryos with 10 volumes of TRIZOL™ reagent (Life Technologies, Gaithersburg, Md.) as recommended by the manufacturer. The initial homogenate was centrifuged at 12000×g and the pellet discarded; chloroform extraction was performed twice. Polyadenylated RNA was isolated with Oligotex-dT (Qiagen, Chatsworth, Calif.), and 2.5 µg from each sample (determined spectrophotometrically) was fractionated on formaldehyde-agarose gels (Farrell (1993) RNA Methodologies, Academic Press). Downward alkaline capillary transfer was performed as described (Chomczynski (1992) *Anal. Biochem.* 201:134–139) except that Sarkosyl was omitted from the transfer buffer. RNA was fixed to the membranes by baking at 80° C. for two hours followed by UV crosslinking. All blots were stained with methylene blue to confirm consistent loading and RNA integrity. Probes were labeled to >2×10$^9$ CPM/µg with [α-$^{32}$P]dCTP and hybridized in Express HIB™ (Clontech, Palo Alto, Calif.) as recommended by the manufacturer. Relative levels of expression were assessed with a Phosphorimager (Molecular Dynamics, Sunnyvale, Calif.). All reported analyses are representative of at least three separate experiments.

Hybridization In Situ

The procedures outlined by Harland (Harland (1991) *Method Cell Biol.* 36:685–695) were followed, except that Boehringer blocking reagent was used (Lamb, et al. (1993) *Science* 262:713–718) and the stained embryos were fixed in Bouin's solution overnight and washing in TRIS-buffered 70% ethanol until background reached negligible levels (Smith and Harland (1992) *Cell* 70:829–840). In some experiments, BM-Purple (Boehringer Mannheim) was substituted for NBT/BCIP. Sense controls were done for all stages and were negative. Human BMP-3 and Xenopus BMP-7 antisense and sense probes were also run in parallel to assess the possibility of cross reactivity with the most closely related known genes and demonstrated distinct patterns of localization (not shown). Uncleared embryos were photographed using reflected light under both brightfield and darkfield conditions with a Nikon SMZ-U stereomicroscope equipped with a FX35A dark box and UFXII photomicrographic attachment. Embryos cleared in benzyl alcohol/ benzyl benzoate were photographed with a Nikon Microphot FXA under diascopic illumination.

RT-PCR Assays

Separate of embryos of embryos of embryo pieces were prepared from at least two different fertilizations for each condition reported. Total RNA was prepared as described above and treated with DNase (Amplification Grade, Life Technologies, Gaithersburg, Md.); reverse transcription was done with Superscript II (Life Technologies, Gaithersburg, Md.) as described by the manufacturer with 1 µg total RNA per reaction. Amplification was performed in 25 µL reactions containing 1×PCR buffer (Perkin Elmer, Norwalk, Conn.), 200 µM dNTPs, 1 µM each primer, 1 U Taq polymerase (Perkin Elmer, Norwalk, Conn.) and 1 µCi [α-$^{32}$P]dCTP. Cycling parameters were 94° C., 30 seconds; 55° C. 30 seconds; 72° C., 1 minute for each cycle; a Model PTC-100 (MJ Research, Watertown, Mass.) was used in all experiments. Assays were calibrated as described by Rupp and Weintraub (Rupp and Weintraub (1991) *Cell* 65:927–937). Optimal cycle numbers were first determined for histone H4 (Niehrs, et al. (1994) *Science* 263:817–820), and input cDNA for each sample was normalized to this marker. PCR conditions for each primer set were then chosen within the linear amplification range. The primer sets used and the number of amplification cycles for each are presented in Table 1 (SEQ ID NOs:8–39). Primers were taken from the indicated references (citations given hereinabove), or designed from sequences specified by accession numbers with GeneWorks (Intelligenetics, Mountain View, Calif.). F and R refer to the forward, or sense, and reverse, or antisense, primers.

TABLE 1

OLIGONUCLEOTIDES USED FOR RT-PCR ASSAY

| Marker | Sequences | SEQ ID NO: | Cycles | Product Size (bp) | Source |
|---|---|---|---|---|---|
| XBra | F 5'-GCTGGAAGTATGTGAATGGAGA-3' | 8 | | | |
|  | R 5'-TTTAAGTGCTGTAATCTCTTCA-3' | 9 | 26 | 318 | (Niehrs et al. 1994) |
| XTwist | F 5'-AGTCCGATCTCAGTGAAGCG-3' | 10 | | | |
|  | R 5'-AGTCGATGTATCTGGAGGCC-3' | 11 | 302 | 26 | M27730 |
| XHox-3 | F 5'-CTCGCATGTCTTAGTACCTCAACCAAC-3' | 12 | | | |
|  | R 5'-GTCATATCTTCCCTCTG-3' | 13 | 32 | 431 | D10455 |
| XMyoD-a | F 5'-AGCTCCAACTGCTCCGACGGCATGAA-3' | 14 | | | |
|  | R 5'-AGGAGAGAATCCAGTTGATGGAAACA-3' | 15 | 28 | 394 | (Rupp et al. 1991) |
| XMyoD-b | F 5'-AACTGCTCCGATGGCATGATGGATTA-3' | 16 | | | |
|  | R 5'-ATTGCTGGGAGAAGGGATGGTGATTA-3' | 17 | 24 | 90 | (Rupp et al. 1991) |
| XAR1 | F 5'-TGTTGCGAATAATCGGAGC-3' | 18 | | | |
|  | R 5'-TTATGTCCAGCAACTGCAGC-3' | 19 | 26 | 700 | M88594 |
| XWnt-8 | F 5'-ATGGACTTCGAAGTGCAACC-3' | 20 | | | |
|  | R 5'-ATGGCTCCTCTGTTGTCAGC-3' | 21 | 26 | 483 | X57234 |
| Noggin | F 5'-CTAAGTAGCCAGAGGGACGAG-3' | 22 | | | |
|  | R 5'-ACACAGCTGCACAAAATAAG-3' | 23 | 30 | 579 | M98807 |
| Goose- | F 5'-AGATTACAGCGGATTTTA-3' | 24 | | | |
| coid | R 5'-CTGGGTACTTGGTTTCT-3' | 25 | 28 | 590 | (Niehrs et al. 1994) |
| ADMP-1 | F 5'-TATTGAGGAACCACCACAGC-3' | 26 | | | |
| (total) | R 5'-CTTATCTGGCAGAAGTGGTGC-3' | 27 | 28 | 297 | The present invention |
| ADMP-1 | F 5'-GAGCTGCAGCTTGATGAG-3' | 28 | | | |
| (endo- | R 5'-GCCACAGTCCAGAGGTTA-3' | 29 | 28 | 371 | The present invention |
| genous) | | | | | |
| Folli- | F 5'-CAATAGAGTCCGGACTTGTGC-3' | 30 | | | |
| statin | R 5'-TACAGAACCTGACATCGGCC-3' | 31 | 30 | 220 | (Hemmati-Brivanlou et al. 1994) |
| NCAM | F 5'-CACAGTTCCAACCAAATGC-3' | 32 | | | |
|  | R 5'-GGAATCAAGCGGTACAGA-3' | 33 | 28 | 342 | (Hemmati-Brivanlou et al. 1994) |
| Muscle | F 5'-GCTGACAGAATGCAGAAG-3' | 34 | | | |
| actin | R 5'-TTGCTTGGAGGAGTGTGT-3' | 35 | 24 | 222 | (Hemmati-Brivanlou et al. 1994) |
| Cardiac | F 5'-TCCCTGTACGCTTCTGGTCGTA-3' | 36 | | | |
| actin | R 5'-TCTCAAAGTCCAAAGCCACATA-3' | 37 | 26 | 252 | (Niehrs et al. 1994) |
| Histone | F 5'-CGGGATAACATTCAGGGTATCACT-3' | 38 | | | |
| H4 | R 5'-ATCCATGGCGGTAACTGTCTTCCT-3' | 39 | 22 | 188 | (Niehrs et al. 1994) |

PCR products were separated on 5% acrylamide gels, dried and exposed to phosphor screens (Molecular Dynamics, Sunnyvale, Calif.) or Kodak XAR film for 0.5–10 hours. PCR analysis was performed at least twice for each cDNA to confirm that the amplifications were reproducible.

Localization of Gene Expression

Figure 4A:
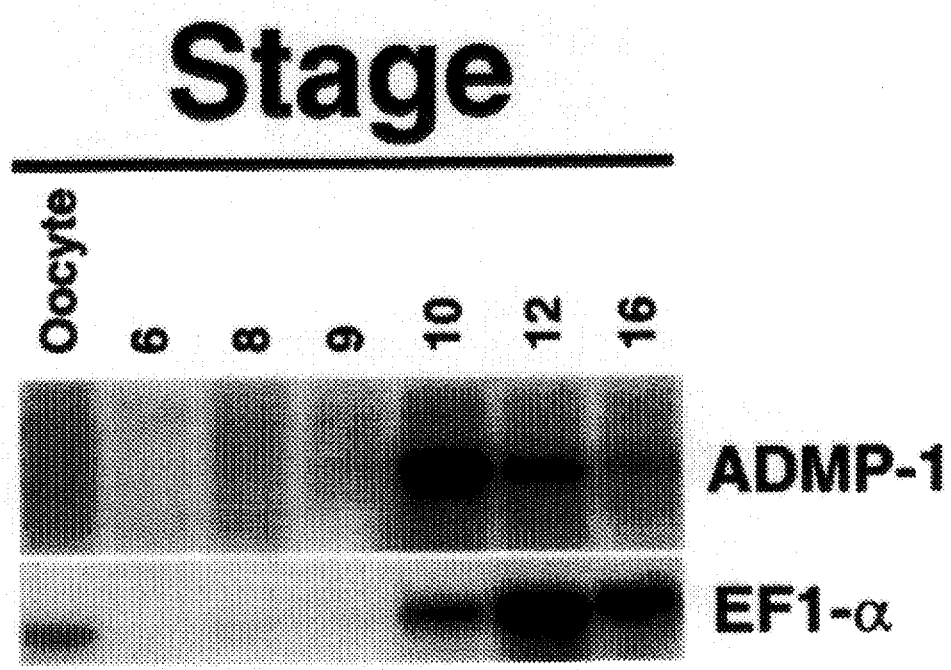
FIG. 4 shows expression of ADMP-1 During Xenopus Development. (A) Developmental Northern blot using 2.5 μg poly (A+) RNA per lane. (B) ADMP-1 present in the dorsal marginal zone during gastrulation. The RNAs from each were analyzed for ADMP-1 by RT-PCR.

FIG. 4A demonstrates that ADMP-1 is undetectable on poly(A+) Northern blots until gastrulation (stage 10), when its expression level increases suddenly and transiently; by stage 12, the expression level decreases markedly. In FIG. 4A showing developmental Northern blot using 2.5 μg poly (A+) RNA per lane, the blot was probed with a 1.4 kb fragment of ADMP-1 cDNA (bp 84–1521); a single 2.2 kb transcript was detected. Translation elongation factor (EF1-α) (Krieg, et al. (1989) Dev Biol. 133, 93–100) and histone H4 were used as controls to confirm consistent RNA loading. The embryonic stages are 6, 8, and 9, blastula; 10 and 12, early and late gastrula; and 16, mid neurula. No transcripts could be detected at later stages (data not shown). This analysis was performed four times with similar results. Hybridization in situ reveals expression throughout the animal region beginning at stage 9, with more concentrated localization at the Spemann organizer by stage 10. As neurulation proceeds, staining becomes restricted to a streak extending anteriorly from the dorsal lip of the blastopore, and follows the development of the neural folds.

Figure 4B:
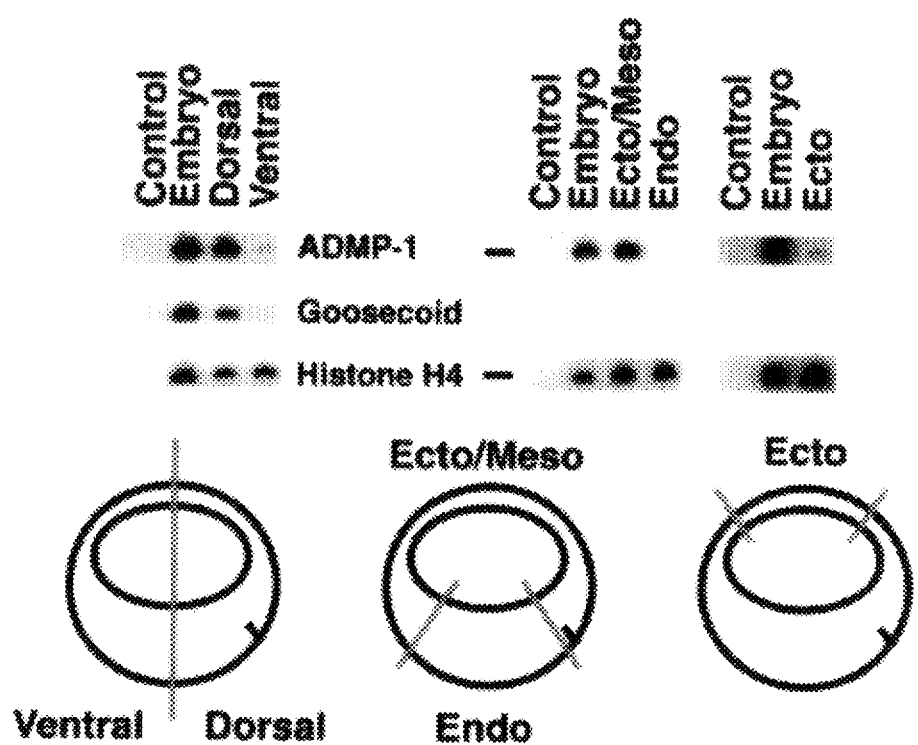

To evaluate the possibility of endodermal expression not detectable by hybridization histochemistry (Bolce, et al. (1993) Dev. Biol. 160:413–423), expression of ADMP-1 in various portions of stage 10.5 embryos was compared by RT-PCR; these results are presented in FIG. 4B. Essentially all of the message is in the dorsal marginal zone. In FIG. 4B, showing ADMP-1 is present in the dorsal marginal zone during gastrulation, stage 10.5 embryos were dissected as indicated in the figure. The RNAs from each were analyzed for ADMP-1 by RT-PCR. The template amounts were normalized to produce approximately equal amounts of histone H4 product (Niehrs, et al. (1994) Science 263:817–820). Goosecold was used as a control for the dorsal vs. ventral dissection, and template from which reverse transcriptase was omitted was used to confirm absence of contaminating genomic DNA sequences (indicated as Control in the figure).

RNA blot analysis revealed a single hybridization signal at much lower stringency than that used for hybridization in situ. This result, together with the RT-PCR analysis and the observation that even closely similar genes such as the Xenopus forkhead homeobox genes XFKH1 (Dirksen and Jamrich (1992) Genes Dev. 6:599–608) and XFKH2 appear not to cross hybridize in whole mounts (Bolce, et al. (1993) Dev. Biol. 160:413–423), indicates that localization of gene expression is adequately reflected by hybridization in situ.

EXPERIMENT 4

Analysis of Activity of ADMP-1 mRNA Injection Experiments

Capped mRNAs were synthesized with mMessage mMachine™ SP6 kits (Ambion, Austin, Tex.) from linearized plasmids, checked for integrity by denaturing agarose electrophoresis (Farrell (1993) RNA Methodologies, Academic Press), and purified by chromatography on DEPC-100 spin columns (Clontech, Palo Alto, Calif.) followed by precipitation and washing with 70% ethanol. They were air dried and redissolved in diethylpyrocarbonate treated water, quantitated by spectrophotometry, and diluted to appropriate final concentrations with injection buffer (88 mM NaCl, 15 mM TRIS-CHl, pH 7.5 (Kay (1991) *Methods Cell Biol.* 36:663–669)). The preprolactin transcription plasmid was prepared as described by Amaya, et al. (*Cell* 66:257–270 (1991)), the nuclear β-galactosidase plasmid was as described by Smith and Harland (*Cell* 67:753–765 (1991)), and the activin plasmid was as constructed by Sergei Sokol (Sokol, et al. (1991) *Cell* 67:741–752).

For injection, embryos as incubated in 1×MMR supplemented with 5% Ficoll 400 (Molecular Biology Grade, Sigma, St. Louis) and gentamycin. Single blastomeres were injected into 2 cell or 8 cell embryos at various sites. When the embryos reached stage 5–6 they were transferred to 0.1×MMR plus gentamycin. Analysis of abnormal phenotypes was based on experiments where the overall viability of injected embryos was at least 90%. Each treatment group contained over 40 viable embryos, and reported results are based on at least four separate experiments. The phenotypic abnormalities displayed in FIGS. 4 and 5 were observed consistently in over ten experiments in which noninjected embryos and preprolactin injected embryos developed normally. Dorsal and ventral regions of the embryos were identified by pigment variations (Nieuwkoop and Faber (1967) Normal table of *Xenopus laevis*, North Holland).

Lineage Tracing

Embryos were injected with 600 pg mRNA encoding β-galactosidase (Smith and Harland (1991) *Cell* 67:753–765) and either preprolactin mRNA or ADMP-1 mRNA as described above. They were fixed for one hour in 1×PBS containing 2% formaldehyde, 0.2% glutaraldehyde, 0.02% NP-40, and 0.1% sodium deoxycholate. They were then stained for β-galactosidase as described by Amaya, et al. (Amaya, et al. (1993) *Development* 118:477–487).

Embryo Perturbations

Dejellied embryos were irradiated with 100000 μJ in a Stratalinker (Stratagene, La Jolla, Calif.) 20 minutes after fertilization in a quartz-bottomed dish (Smith and Harland (1991) *Cell* 67:753–765) and cultured in 0.1×MMR plus gentamycin. Embryos as the 32 cell stage were transferred to 0.1M LiCl in 0.1×MMR plus gentamycin for 60 minutes, washed three times with 0.1×MMR plus gentamycin, and cultured in this medium (Kao and Elinson (1988) *Dev. Biol.* 127:64–77).

Analysis of Ventralizing Activity of ADMP-1

Figure 5A:
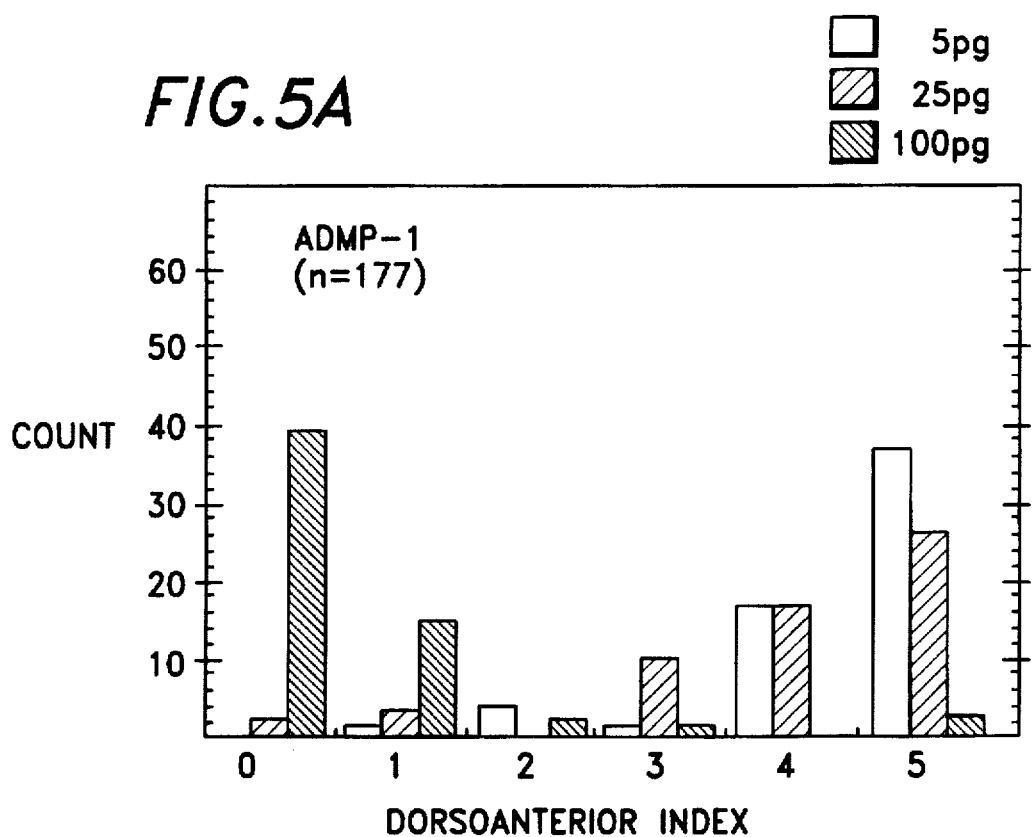
FIG. 5 shows frequency histogram of Dorsoanterior Index scores of embryos at 5, 25, and 100 pg injected mRNA comparing the effects of ADMP-1 and preprolactin.
Figure 5B:
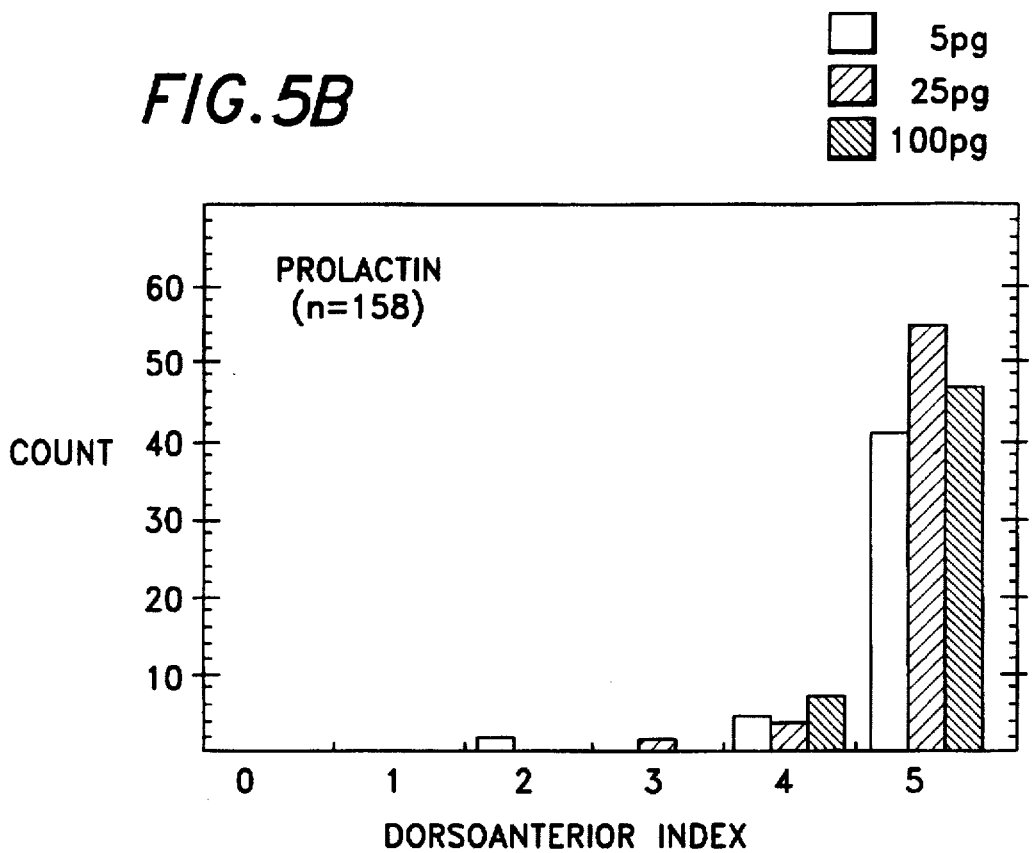

Injection of ADMP-1 mRNA into dorsal but not ventral blastomeres at the 8-cell stage produced a range of ventralized phenotypes. The most prominent abnormalities are suppression of anterior-dorsal structures, anterior hypopigmentation, gut dysgenesis, and dysmotility. Despite these severe morphologic defects, a normally beating heart developed in the majority of embryos at the 25 pg dose. The effect was dose-dependent; the frequency distribution of various Dorsoanterior Index (DAI, (Kao and Elinson (1988) *Dev. Biol.* 127:64–77)) scores at different doses is shown in FIG. 5. In this Figure, the mean DAI scores of ADMP-1 and preprolactin injected embryos differ significantly (p<0.01) at all doses. The data shown are representative of four experiments with comparable numbers of embryos, and at least ten experiments overall. Some variation in sensitivity to injected ADMP-1 message was observed between different batches of embryos. Nearly all embryos injected with preprolactin message developed normally at all doses tested. Despite the profound phenotypic alterations observed at later stages, no gross morphologic abnormalities were observed prior to neurulation at a 100 pg dose of ADMP-1 mRNA. In particular, no abnormalities in blastopore closure, which can indicate nonspecific toxic effects, were apparent in either control or ADMP-1 injected embryos.

To confirm that these effects were not due merely to ablation of injected cells, and assess alterations in cell fate following injection, mRNA encoding β-galactosidase was coinjected with either ADMP-1 or preprolactin message. It is demonstrated that the progeny of ADMP-1 injected cells remained viable, and that many were converted to a ventral fate when compared with controls. Milder phenotypes often showed staining in somites which appeared moderately enlarged and disordered. More severely perturbed embryos showed nearly complete disruption of the regular somitic distribution of β-galactosidase staining seen in controls. Many ventral cells were positive for β-galactosidase stain in these embryos.

EXPERIMENT 5

ADMP-1 Expression Influenced by LiCl, Activin and UV Irradiation

Figure 6A:
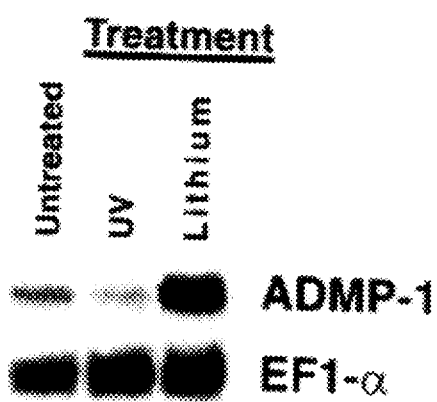
FIG. 6 shows induction of ADMP-1 by LiCl and Activin. (A) Northern blots of poly(A+) RNA from untreated, UV-irradiated or LiCl treated embryos (see methods). (B) RT-PCR assay for ADMP-1 in animal caps from untreated embryos or embryos injected with mRNA encoding either preprolactin or activin.
Figure 6B:
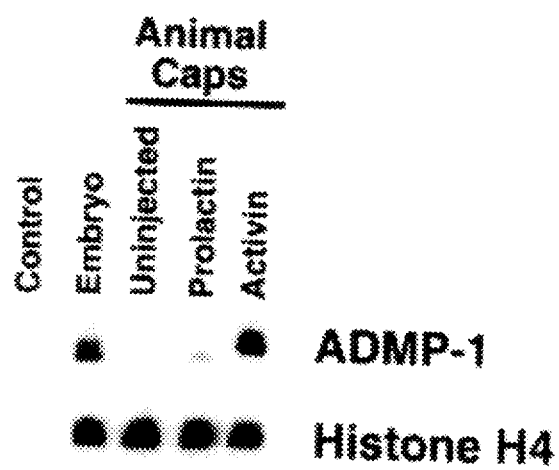

Perturbations of embryonic axis formation by various means (Kao and Elinson (1988) *Dev. Biol.* 127:64–77) have become invaluable for characterizing the activities of molecules regulating the body axis. Accordingly, we evaluated the effects of lithium chloride, which dorsalizes embryos, and UV irradiation, which ventralizes them, on expression of ADMP-1. Lithium treatment produced a ten fold increase in ADMP-1 mRNA levels, while UV irradiation resulted in a 2–3 fold decrease (FIG. 6A). In FIG. 6A, UV irradiation decreased expression of ADMP-1; LiCl induced expression. EFI-α (Krieg, et al. (1989) *Dev. Biol.* 133:93–100) was used as a loading control. This experiment was performed four times. When embryos were injected with ADMP-1 mRNA and subsequently treated with lithium, the dorsalizing effect of the latter was markedly reduced, and several ventralized embryos resulted; control embryos injected with preprolactin mRNA before lithium treatment were all dorsalized to the same extent as noninjected embryos (not shown). Injection of activin message, which is known to induce dorsal tissues and markers (Sokol, et al. (1990) *Science* 249:561–564; Thomsen, et al. (1990) *Cell* 63:485–493), increased ADMP-1 expression by over ten fold (FIG. 6B). In FIG. 6B showing RT-PCR assay for ADMP-1 in animal caps from untreated embryos or embryos injected at the 2 cell stage with 1 ng mRNA encoding either preprolactin or activin; the latter resulted in a pronounced increase in ADMP-1 expression. Histone H4 was used to normalize between samples (Niehrs, et al. (1994) *Science* 263:817–820). As in FIG. 4, template from which reverse transcriptase was omitted was used to confirm absence of contaminating genomic DNA sequences.

EXPERIMENT 6

Figure 7B:
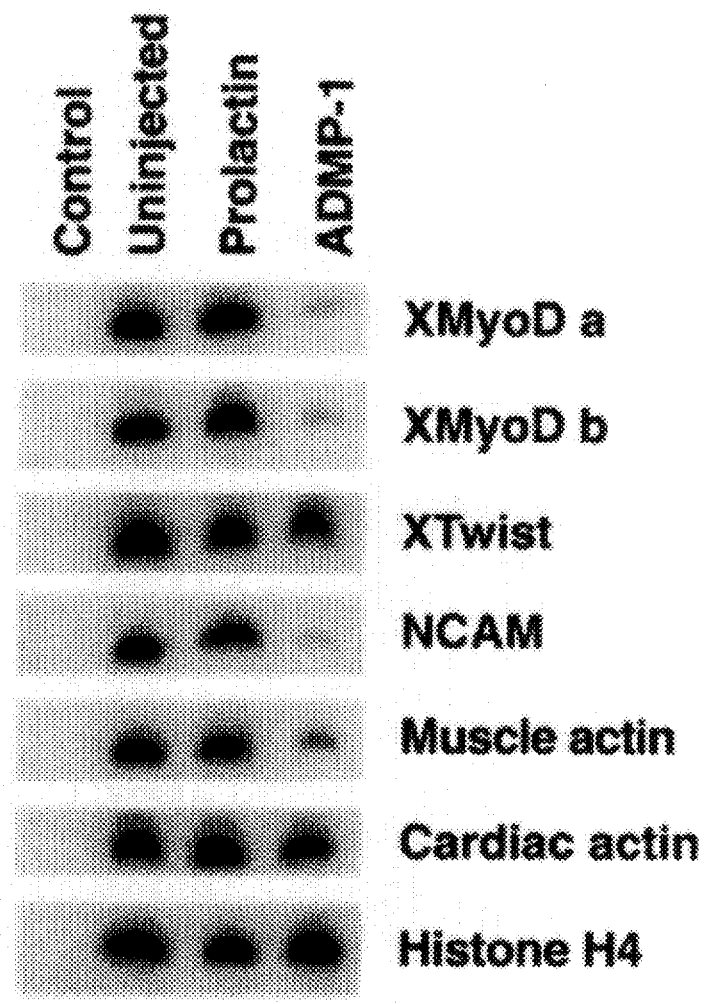
Figure 7C:
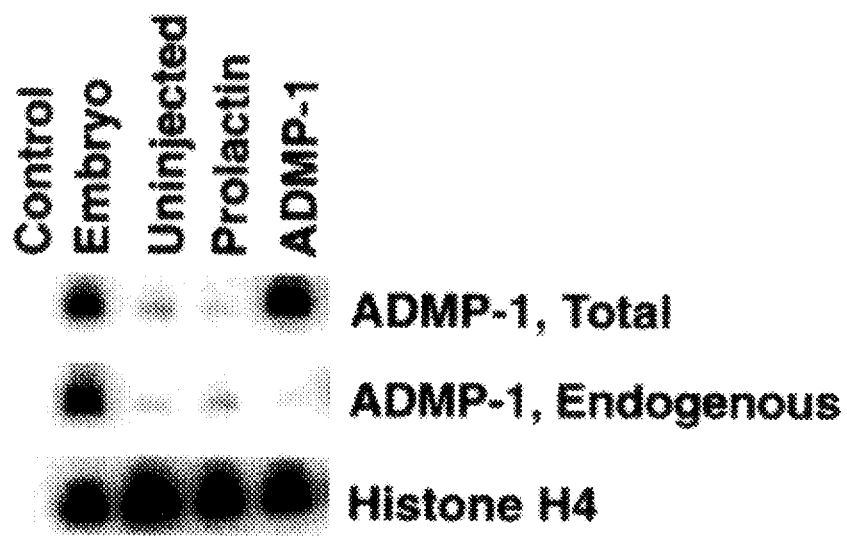

Suppressing Effects of ADMP-1 on Expression of Noggin, Goosecold, Follistatin, NCAM and Muscle Actin To explore the molecular consequences of ADMP-1 overexpression, various signaling molecules and markers were assessed by RT-PCR in stage 10.5 (FIGS. 7A and 7C) or stage 17 (FIG. 7B) embryos injected with ADMP-1, preprolactin, or activin mRNA. In FIG. 7, stage 10 (A) or stage 17 (B) embryos were assayed for expression in the indicated genes by RT-PCR following injection of 1 ng ADMP-1 message into one blastomere of 2 cell embryos. In (C), total ADMP-1 in animal cap is assayed with primers that are both within the open reading frame, so that injected as well as endogenous ADMP-1 message are detected. For endogenous ADMP-1, one primer is from a region outside the open reading frame; the injected mRNA is thus not amplified. Total RNA from pools of 20 embryos or caps was the template for cDNA synthesis in each case. Control indicates template from which reverse transcriptase was omitted to confirm absence of contaminating genomic DNA sequences. Injection of ADMP-1 mRNA caused profound suppression of the dorsalizing signals noggin, goosecold, and follistatin, as well as the activin receptor. Dorsal markers, including XMyoD, NCAM, and muscle actin, were also strongly downregulated. Suppression of other markers was less pronounced. Overexpression of ADMP-1 was confirmed by RT-PCR analysis as shown in FIG. 7C.

We claim:

1. An isolated polynucleotide encoding an anti-dorsalizing morphogenetic protein having the sequence indicated as SEQ ID NO:1.

2. An isolated recombinant anti-dorsalizing morphogenetic protein obtained by expression of a polynucleotide having the sequence indicated as SEQ ID NO:1.

3. An isolated recombinant anti-dorsalizing morphogenetic protein, wherein said protein has the amino acid sequence indicated as SEQ ID NO: 2.

4. A polynucleotide isolated from a mammalian genomic DNA or cDNA library that encodes a native anti-dorsalizing morphogenetic protein that has at least 90% amino acid identity to the sequence indicated as SEQ ID NO: 2.

5. A polynucleotide according to claim 4, wherein the polynucleotide has a sequence from human DNA.

6. A composition, comprising an isolated recombinant antidorsalizing morphogenetic protein having the amino acid sequence indicated as SEQ ID NO:2 or a native anti-dorsalizing morphogenetic protein having at least 90% amino acid identity therewith, and a carrier.

* * * * *